US012263168B2

(12) United States Patent
Siracusa

(10) Patent No.: US 12,263,168 B2
(45) Date of Patent: Apr. 1, 2025

(54) CARBONIC ANHYDRASE ENZYMES FOR REGULATING MAST CELL HEMATOPOIESIS AND TYPE 2 INFLAMMATION

(71) Applicant: Rutgers, the State University of New Jersey, New Brunswick, NJ (US)

(72) Inventor: Mark C. Siracusa, New Brunswick, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 17/855,501

(22) Filed: Jun. 30, 2022

(65) Prior Publication Data
US 2023/0149403 A1 May 18, 2023

Related U.S. Application Data

(62) Division of application No. 16/940,677, filed on Jul. 28, 2020, now Pat. No. 11,406,637, which is a division of application No. 15/764,785, filed as application No. PCT/US2016/046819 on Aug. 12, 2016, now Pat. No. 10,758,537.

(60) Provisional application No. 62/235,257, filed on Sep. 30, 2015.

(51) Int. Cl.
| | |
|---|---|
| *A61K 31/513* | (2006.01) |
| *A61K 31/18* | (2006.01) |
| *A61K 31/4184* | (2006.01) |
| *A61K 31/423* | (2006.01) |
| *A61K 31/433* | (2006.01) |
| *A61K 31/451* | (2006.01) |
| *A61K 31/505* | (2006.01) |
| *A61K 31/542* | (2006.01) |
| *A61K 31/7048* | (2006.01) |
| *A61K 45/06* | (2006.01) |
| *A61P 11/06* | (2006.01) |

(52) U.S. Cl.
CPC ............ *A61K 31/513* (2013.01); *A61K 31/18* (2013.01); *A61K 31/4184* (2013.01); *A61K 31/423* (2013.01); *A61K 31/433* (2013.01); *A61K 31/451* (2013.01); *A61K 31/505* (2013.01); *A61K 31/542* (2013.01); *A61K 31/7048* (2013.01); *A61K 45/06* (2013.01); *A61P 11/06* (2018.01); *A61K 2300/00* (2013.01)

(58) Field of Classification Search
None
See application file for complete search history.

(56) References Cited

U.S. PATENT DOCUMENTS

| | | | |
|---|---|---|---|
| 5,366,967 A | * | 11/1994 | Bianco .................. A61K 45/06 514/59 |
| 10,758,537 B2 | | 9/2020 | Siracusa |
| 11,406,637 B2 | | 8/2022 | Siracusa |
| 2003/0149090 A1 | | 8/2003 | Gehlsen et al. |
| 2008/0242646 A1 | | 10/2008 | Lessem et al. |
| 2013/0028864 A1 | | 1/2013 | Theoharides et al. |
| 2015/0266900 A1 | | 9/2015 | Matulis et al. |

FOREIGN PATENT DOCUMENTS

| | | |
|---|---|---|
| WO | 2007067036 A2 | 6/2007 |
| WO | 2013040206 A1 | 3/2013 |

OTHER PUBLICATIONS

O'Donnell et al (Am Rev Respir Dis 146:1518-1523, 1992) (Year: 1992).*
Carta et al (Expert Opin Ther Patents, 11 pages, 2013) (Year: 2013).*
Cadwallader et al (Brit J Pharmacol 161:1-16, 2010) (Year: 2010).*
Methazolamide Product Monograph (Jul. 10, 2010) (Year: 2010).*
Allen, J E , et al., "Diversity and dialogue in immunity to helminths. ", Nat Rev Immunol 11, 375-388 (2011).
Allen, J E , et al., "Host protective roles of type 2 immunity: Parasite killing and tissue repair, flip sides of the same coin.", Semin Immunol 26, 329-340 (2014).
Anthony, R M , et al., "Protective immune mechanisms in helminth infection.", Nat Rev Immunol 7(12), 975-987 (2007).
Bauer, R N , et al., "The Future of Biologics: Applications for Food Allergy.", J Allergy Clin Immunol 135(2), 312-323 (2015).
Capkauskaite, E. , et al., "Design of [(2-pyrimidinylthio)acetyl] benzenesulfonamides as inhibitors of human carbonic anydrases", European Journal of Medicinal Chemistry 51, 259-270 (2012).
Dahlin, J , et al., "Mast cell progenitors: Origin, development and migration to tissues", Mol Immunol 63 (1), 9-17 (2015).
Ekinci, D , et al., "Carbonic anhydrase inhibitors: in vitro inhibition of alpha isoforms (hCAI, hCA II, bCA III, hCAIV) by flavonoids", Journal of Enzyme Inhibition and Medicinal Chemistry 28(2), 283-288 (2013).
Frieri, M , et al., "Comparison of the therapeutic efficacy of cromolyn sodium with that of combined chlorpheniramine an dcimetidine in systemic mastocytosis. Results of a double-blind clinical trial.", Am J Med 78(1), 9-14 (1985).
Gause, W C , et al., "Type 2 immunity and wound healing: evolutionary refinement of adaptive immunity by helminths.", Nat Rev Immunol 13(8), 607-614 (2013).
Geerts, S , et al., "Drug Resistance in Human Helminths: Current Situation and Lessons from Livestock.", Clin Microbiol Rev 13, 207-222 (2000).

(Continued)

*Primary Examiner* — Craig D Ricci
(74) *Attorney, Agent, or Firm* — Viksnins Harris Padys Malen LLP

(57) ABSTRACT

The invention provides methods and compositions that are useful for treating allergic diseases, bacterial infections, fungal infections, viral infections, mastocytosis, mast cell-mediated inflammation and parasite infections (e.g., helminth infections).

8 Claims, 6 Drawing Sheets

Specification includes a Sequence Listing.

(56) References Cited

OTHER PUBLICATIONS

Henry, E, et al., "Carbonic anhydrase enzymes regulate mast cell-mediated inflammation", J Exp Med 213(9), 1663-1673 (2016).

Inclan-Rico, J, et al., "Trichinella spiralis-induced mastocytosis and erythropoiesis are simultaneously supported by a bipotent mast cell/erythrocyte precursor cell", PLoS Pathogens 16(5), e1008579 (2020).

Jia, T-W, et al., "Soil-Transmitted Helminth Reinfection after Drug Treatment: A Systematic Review and Meta-Analysis.", PLoS Negl Trop Dis 6, e1621 (2012).

Patent Cooperation Treaty, International Searching Authority, Search Report and Written Opinion for PCT/US2016/046819, 11 pages, Oct. 31, 2016.

Pawankar, R, et al., "WAO White Book on Allergy 2011-2012: Executive Summary.", World Allergy Organization (2012).

Pulendran, B, et al., "New Paradigms in Type 2 Immunity.", Science 337(6093), 431-435 (2012).

Sarikaya, et al., "Carbonic Anhydrase Inhibitors: Inhibition of Human Erythrocyte Isozomes I and II with a Series of Phenolic Acids", Chem. Biol. Drug Des 75, 515-520 (2010).

Seguin, B, et al., "The danger hypothesis applied to idiosyncratic drug reactions", Current Opinion in Allergy and Clinical Immunology 3(4), 235-242 (2003).

Stepan, A, et al., "Structural alert/reactive metabolite concept as applied in medicinal chemistry to mitigate the risk of idiosyncratic drug toxicity: a perspective based on the critical examination of trends in the top 200 drugs marketed in the United States", Chemical Research in Toxicology 24(9), 1345-1410 (2011).

Talibov, V O, et al., "Kinetically Selective Inhibitors of Human Carbonic Anhydrase Isozymes I, II, VII, IX, XII, and XIII.", J Med Chem 59, 2083-2093 (2016).

Uetrecht, J, "Idiosyncratic drug reactions: past, present, and future", Chemical Research in Toxicology 21(1), 84-92 (2008).

Voehringer, D, "Protective and pathological roles of mast cells and basophils.", Nat Rev Immunol 13(5), 362-375 (2013).

Weng, Z, et al., "Quercetin is More Effective than Cromolyn in Blocking Human Mast Cell Cytokine Release and Inhibits Contact Dermatitis and Photosensitivity in Humans", PLoS One 7(3), 33805, 10 pages (2012).

Winum, J, "Carbonic anhydrase enzymes for regulating mast cell hematopoiesis and type-2 inflammation: a patent evaluation (WO2017/05870).", Expert Opinion on Therapeutic patents 28(10), 741-743 (2018).

\* cited by examiner

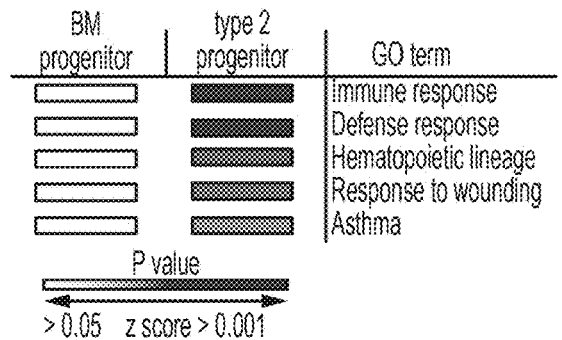
Figure 1A
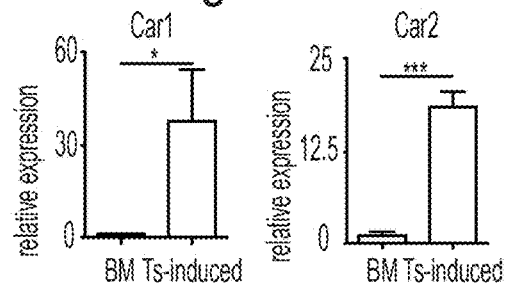
Figure 1B
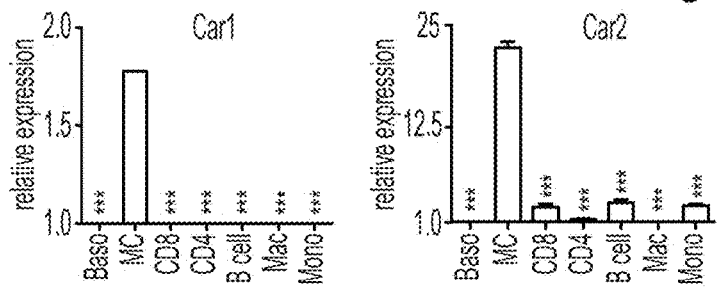
Figure 1C
Figure 1D
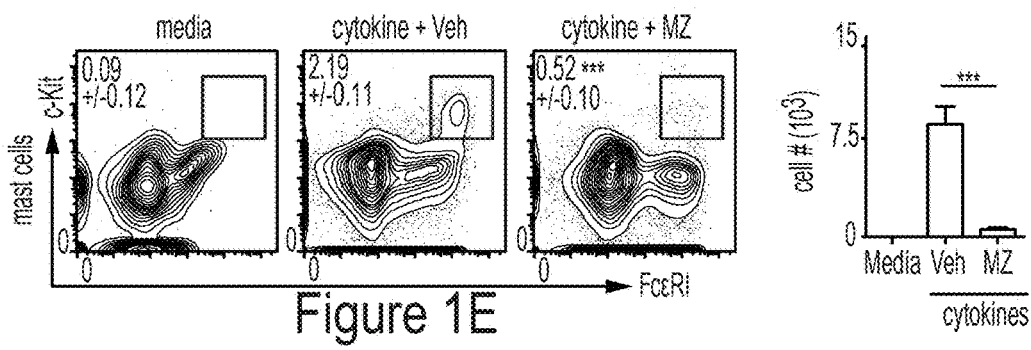
Figure 1E
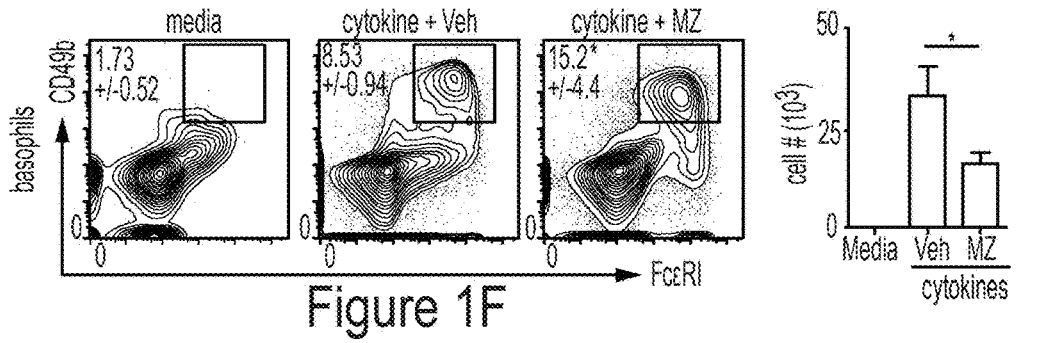
Figure 1F

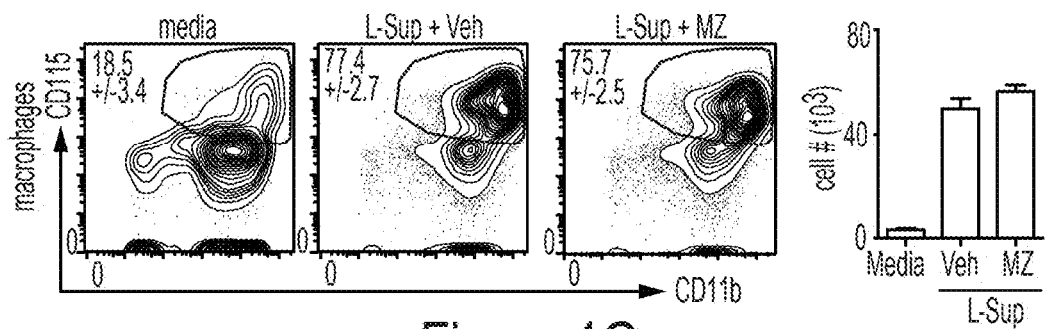
Figure 1G
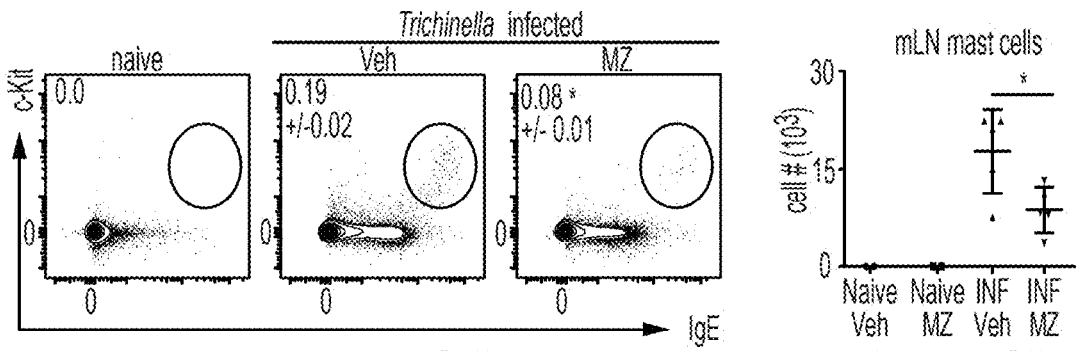
Figure 2A
Figure 2B
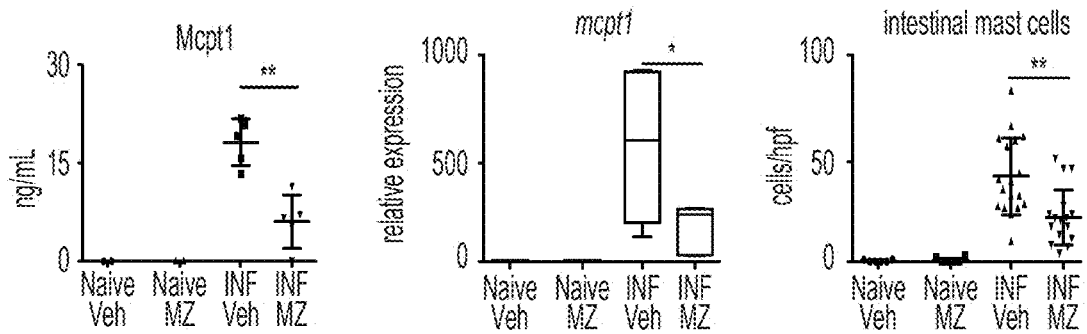
Figure 2C
Figure 2D
Figure 2E
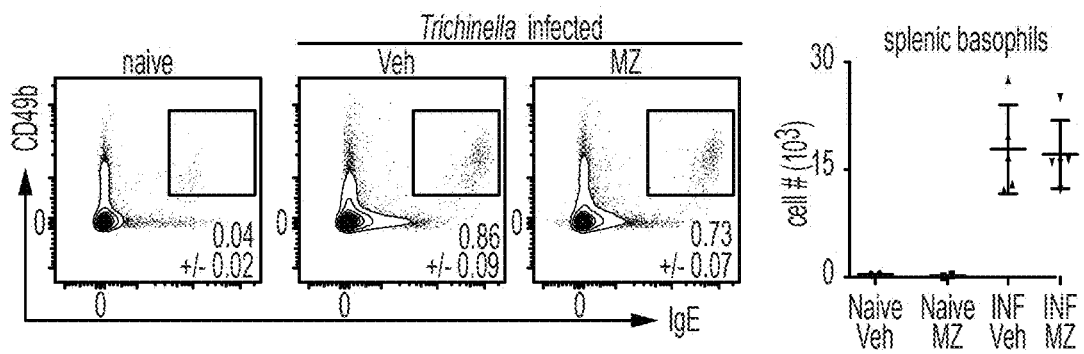
Figure 2F
Figure 2G

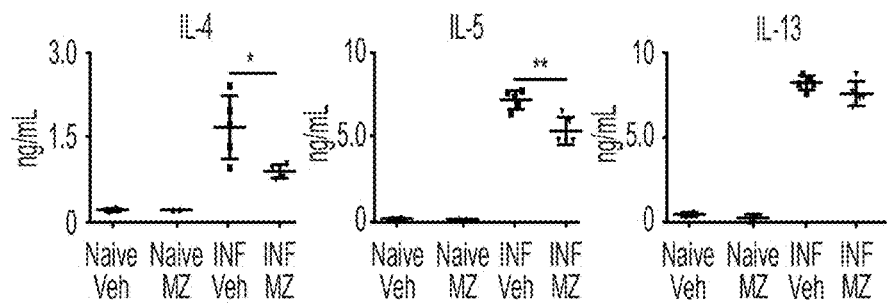
Figure 3A
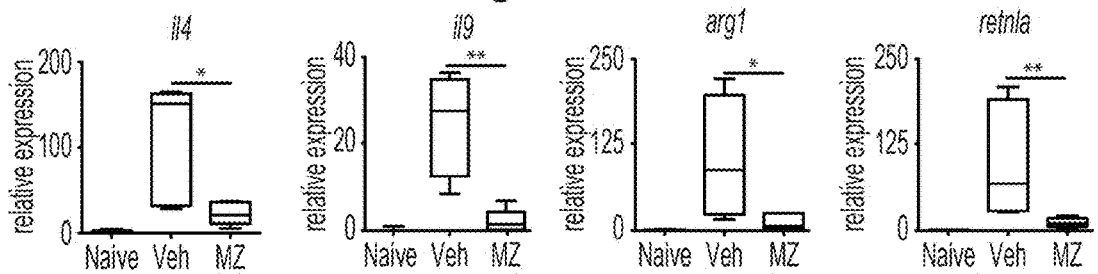
Figure 3B
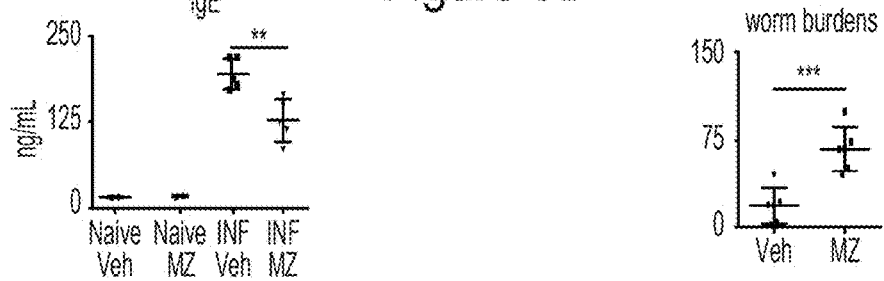
Figure 3C
Figure 3D
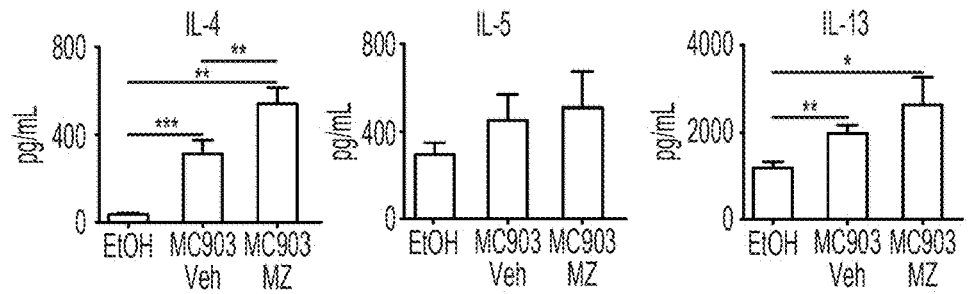
Figure 3E
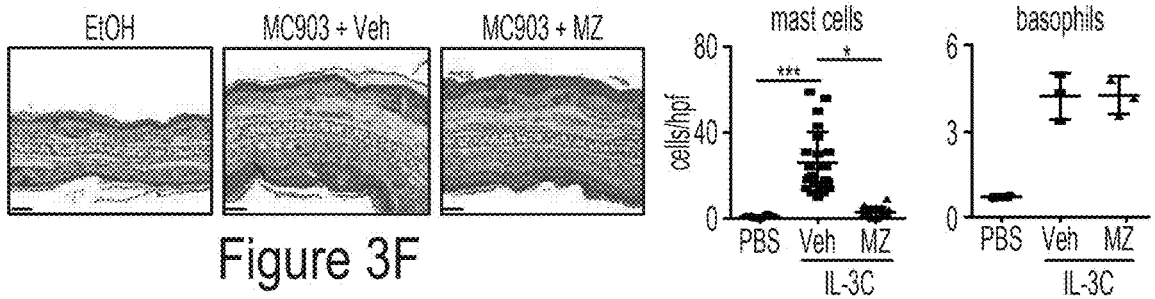
Figure 3F
Figure 3G

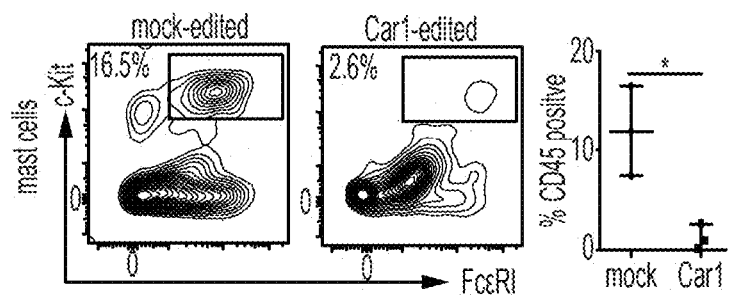
Figure 4J
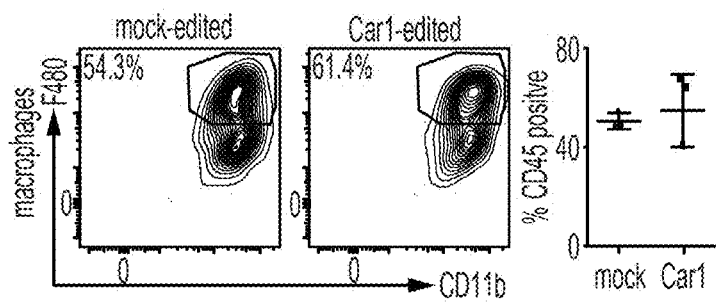
Figure 4K
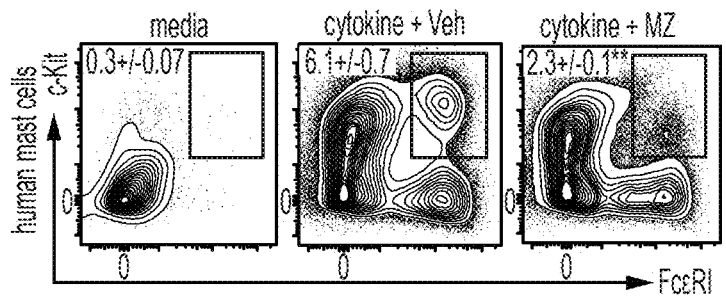
Figure 4L
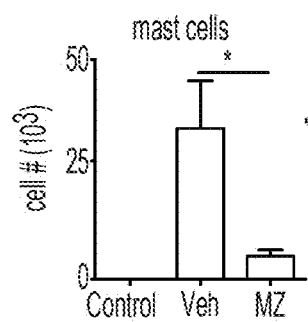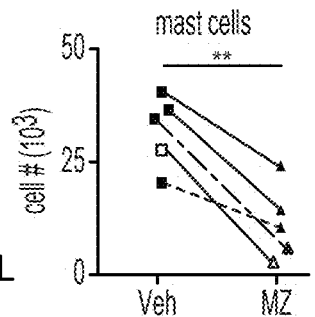
Figure 4M   Figure 4N

CARBONIC ANHYDRASE ENZYMES FOR REGULATING MAST CELL HEMATOPOIESIS AND TYPE 2 INFLAMMATION

CROSS-REFERENCE TO RELATED APPLICATIONS

This application is a divisional of U.S. patent application Ser. No. 16/940,677, filed Jul. 28, 2020, now U.S. Pat. No. 11,406,637, issued Aug. 9, 2022, which is a divisional of U.S. patent application Ser. No. 15/764,785, now U.S. Pat. No. 10,758,537, issued Sep. 1, 2020, which is a 35 U.S.C. § 371 application of International Application No. PCT/US2016/046819, filed Aug. 12, 2016, which claims the benefit of U.S. Provisional Application No. 62/235,257, filed Sep. 30, 2015. The entire content of the applications referenced above is hereby incorporated by reference herein.

STATEMENT OF GOVERNMENT SUPPORT

This invention was made with government support under K22 AI110573-01 and RO1 AI123224 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 29, 2020, is named 08035_085US2_SL.txt and is 1,120 bytes in size.

BACKGROUND

Type 2 immune responses are characterized by the development of T helper type 2 ($T_H2$) cells, interleukin (IL)-4, -5, -9 and -13 expression, basophil and mast cell responses and increased IgE production. Type 2 cytokine-mediated inflammation promotes the development of protective immunity to parasites (e.g., helminth parasites), but is also responsible for the pathology associated with allergies and asthma (Gause, et al., *Nat Rev Immunol* 13, 607-614 (2013); Allen, et al., *Nat Rev Immunol* 11, 375-388 (2011); Anthony, et al., *Nat Rev Immunol* 7, 975-987 (2007); Allen, et al., *Semin Immunol* 26, 329-340 (2014); Pulendran, et al., *Science* 337, 431-435 (2012)). Helminth parasites infect an estimated 2 billion people worldwide and result in abdominal pain, anemia, impaired cognitive ability, retarded growth and exert enormous economic burdens on heavily infected areas (Gause, et al., *Nat Rev Immunol* 13, 607-614 (2013); Allen, et al., *Nat Rev Immunol* 11, 375-388 (2011)). Allergic diseases have risen to epidemic proportions in developed areas of the world and it is now estimated that 30-40% of the global population suffer from one or more allergic diseases including atopic dermatitis, asthma and food allergies (Pawankar, et al., WAO White Book on Allergy 2011-2012: Executive Summary. *World Allergy Organization* (2012)). Current therapeutic strategies to treat helminth infections and their associated morbidities are limited by the rate of reinfection and the increased prevalence of drug resistant parasites (Jia, et al., *PLoS Negl Trop Dis* 6, e1621 (2012); Geerts, et al., *Clin Microbiol Rev* 13, 207-222 (2000)). Similarly, there are limited treatment options for patients suffering from chronic allergic inflammation and many of them have significant side effects (Bauer, et al., *J Allergy Clin Immunol* 135, 312-323 (2015)). Therefore, it is essential that a better understanding of the immune events that promote type 2 responses is obtained in order to aid in the development of new strategies to treat associated diseases, such as parasite infections (e.g., helminth infections) and allergic inflammation (Pulendran, et al., *Science* 337, 431-435 (2012); Bauer, et al., *J Allergy Clin Immunol* 135, 312-323 (2015)). Improved treatment options are also needed.

SUMMARY OF CERTAIN EMBODIMENTS OF THE INVENTION

Accordingly, certain embodiments of the invention provide a method for treating an allergic disease, bacterial infection, fungal infection or viral infection comprising administering to a mammal (e.g., a patient) in need thereof an effective amount of a Car enzyme inhibitor.

Certain embodiments of the invention provide a method for treating mastocytosis comprising administering to a mammal (e.g., a patient) in need thereof an effective amount of a Car enzyme inhibitor.

Certain embodiments of the invention provide a method for treating mast cell-mediated inflammation comprising administering to a mammal (e.g., a patient) in need thereof an effective amount of a Car enzyme inhibitor.

Certain embodiments of the invention provide a Car enzyme inhibitor for use in medical therapy.

Certain embodiments of the invention provide a Car enzyme inhibitor for the prophylactic or therapeutic treatment of an allergic disease, a bacterial infection, a fungal infection, a viral infection, mastocytosis or mast cell-mediated inflammation.

Certain embodiments of the invention provide the use of a Car enzyme inhibitor to prepare a medicament for the treatment of an allergic disease, a bacterial infection, a fungal infection, a viral infection, mastocytosis or mast cell-mediated inflammation in a mammal (e.g., a patient) in need thereof.

Certain embodiments of the invention provide a pharmaceutical composition for use in the prophylactic or therapeutic treatment of an allergic disease, a bacterial infection, a fungal infection, a viral infection, mastocytosis or mast cell-mediated inflammation, comprising a Car enzyme inhibitor, and a pharmaceutically acceptable carrier.

Certain embodiments of the invention provide a formulation comprising a Car enzyme inhibitor and one or more additional therapeutic agents (e.g., an anti-histamine, a steroid, an anti-IgE therapy, a decongestant, a bronchodilator, a mast cell stabilizer, a leukotriene modifier and/or an immunotherapy).

Certain embodiments of the invention provide a combination of a) a Car enzyme inhibitor; and b) one or more additional therapeutic agent(s), for the prophylactic or therapeutic treatment of an allergic disease, a bacterial infection, a fungal infection, a viral infection, mastocytosis or mast cell-mediated inflammation.

Certain embodiments of the invention provide a kit comprising a Car enzyme inhibitor, packaging material, and instructions for administering the Car enzyme inhibitor to a mammal (e.g., a patient) in need thereof to treat an allergic disease, a bacterial infection, a fungal infection, a viral infection, mastocytosis or mast cell-mediated inflammation.

Certain embodiments of the invention provide a method for treating a parasite infection (e.g., a helminth infection) comprising administering to a mammal (e.g., a patient) in need thereof an effective amount of a Car enzyme activator.

Certain embodiments of the invention provide a Car enzyme activator for use in medical therapy.

Certain embodiments of the invention provide a Car enzyme activator for the prophylactic or therapeutic treatment of a parasite infection.

Certain embodiments of the invention provide a use of a Car enzyme activator to prepare a medicament for the treatment of a parasite infection in a mammal (e.g., a patient) in need thereof.

Certain embodiments of the invention provide a pharmaceutical composition for use in the prophylactic or therapeutic treatment of a parasite infection, comprising a Car enzyme activator, and a pharmaceutically acceptable carrier.

Certain embodiments of the invention provide a formulation comprising a Car enzyme activator and one or more additional therapeutic agents.

Certain embodiments of the invention provide a combination of a) a Car enzyme activator; and b) one or more additional therapeutic agent(s), for the prophylactic or therapeutic treatment of a parasite infection.

Certain embodiments of the invention provide a kit comprising a Car enzyme activator, packaging material, and instructions for administering the Car enzyme activator to a mammal (e.g., a patient) in need thereof to treat a parasite infection.

BRIEF DESCRIPTION OF THE FIGURES

FIGS. 1A-1G. Transcriptional profiles of BM-resident or type 2 progenitors were compared. Enriched pathways in type 2 progenitors were identified (FIGS. 1A-1B). Progenitors were purified from the BM of naïve mice or the spleens of $T.$ $spiralis$-infected mice and gene expression determined (FIG. 1C). Cell populations were purified from naïve mice or cell cultures and gene expression (relative to Baso) determined (FIG. 1D). BM-resident progenitors were isolated and cultured with IL-3 or L-sup in the presence of Veh or MZ and mast cells (FIG. 1E), basophils (FIG. 1F), and macrophages (FIG. 1G) were quantified. (FIG. 1C), Results are representative of 3-5 pooled biological replicates. (FIG. 1D), Results are representative of 4 biological replicates. (FIG. 1E-1G), Results are representative of at least 3 individual experiments. Numbers in cytometry plots represent the percentage of cells gated. Statistical analysis performed using a Student's t-test. (*, $p<0.05$), (***, $p<0.001$).

FIGS. 2A-2G. $T.$ $spiralis$-infected mice were treated with Veh or MZ, and mast cells in the mLNs (FIGS. 2A-2B), serum levels of Mcpt1 (FIG. 2C), intestinal expression of mcpt1 (FIG. 2D), intestinal mast cells in histological sections (FIG. 2E), and splenic basophils (FIGS. 2F-2G) were evaluated. Results are representative of at least 3 individual experiments with at least 2 mice per naïve group and at least 3 mice per $T.$ $spiralis$-infected group. Numbers in cytometry plots represent the percentage of cells gated. Statistical analysis performed using a Student's t-test. (*, $p<0.05$), (**, $p<0.01$).

FIGS. 3A-3J. $T.$ $spiralis$-infected mice (INF) were treated with Veh or MZ. Isolated mLN cells were stimulated and levels of IL-4, IL-5 and IL-13 (FIG. 3A), intestinal expression of il4, il9, arg1 and retnla (FIG. 3B), serum IgE levels (FIG. 3C), and worm burdens were evaluated (FIG. 3D). Mice were treated with ethanol (EtOH) or MC903 and Veh or MZ. Skin-draining LN cells were stimulated and levels of IL-4, IL-5 and IL-13 (FIG. 3E) and skin pathology were evaluated (FIG. 3F). Rag1$^{-/-}$ mice were treated with PBS or IL-3C and Veh or MZ. Intestinal mast cells and splenic basophils were evaluated (FIG. 3G). $A.$ $fumigatus$-infected mice were treated with Veh, MZ, or anti-Ly6G and neutrophils responses and lung fungal burdens (FIGS. 3H-3J) determined. (FIGS. 3A-3J), Results are representative of at least 3 independent experiments with at least 2 mice per naïve group and at least 3 mice per experimental group. Statistical analysis performed using a Student's t-test. (*, $p<0.05$), (, $p<0.01$), (*, $p<0.001$). Scale bar=50 µm.

FIGS. 4A-4N. OVA challenged (chal) or sensitized and challenge (sens/chal) mice were treated with Veh or MZ. Serum Mcpt1 (FIG. 4A), intestinal expression of mcpt1 (FIG. 4B), intestinal mast cell populations in histological sections (FIGS. 4C-4D) and serum IgE levels were evaluated (FIG. 4E). Mice were reconstituted with WT and Car2$^{-/-}$ BM (50/50) and the percent chimerism determined (FIG. 4F). Chimeric mice were infected with $T.$ $spiralis$ and mLN mast cells were evaluated (FIGS. 4G-4H). Mice reconstituted with 100 percent WT or 100 percent Car2$^{-/-}$ BM were infected with $T.$ $spiralis$, and intestinal expression of car1 determined (FIG. 4I). Mock-edited or Car1-edited stem cells were cultured under mast cell (FIG. 4J) or macrophage-promoting conditions (FIG. 4K). Human CD34$^+$ cells were cultured with mast cell-promoting cytokines in the presence of Veh or MZ. Representative analysis from one donor (FIGS. 4L-4M). Pooled mast cell numbers from 5 individual donors (FIG. 4N). (FIGS. 4A-4B), Results are illustrated as the combined data sets of 3 independent experiments. (FIGS. 4C-4E), Results are representative of 3 independent experiments of at least 2 mice per chal group and at least 3 mice per sen/chal group. (FIGS. 4F-4H), Results are representative of 2 independent experiments of 9 biological replicates total. (FIG. 4I), Results are representative of 2 independent experiments of 10 biological replicates total. (FIGS. 4J-4K), Results are representative of 3 independent experiments with at least 3 technical replicates per experiment. Numbers in cytometry plots represent the percentage of cells gated. Statistical analysis was performed using a Student's t-test. (*, $p<0.05$), (, $p<0.01$), (*, $p<0.001$). Scale bar=100 µm.

DETAILED DESCRIPTION

Figures 3H, 3I, 3J:
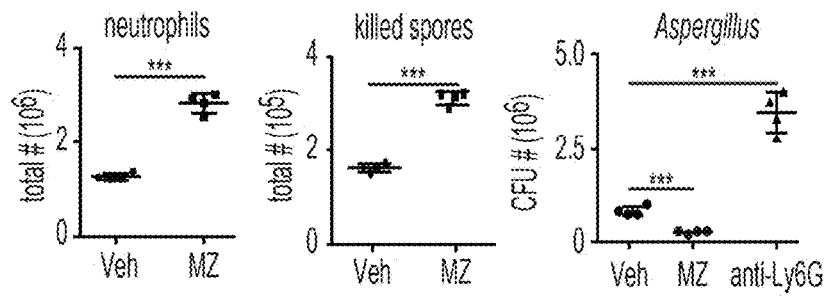

It is well established that type 1 immune responses can be initiated by the recognition of pathogen-associated molecular patterns (PAMPs) via germline-encoded receptors on immune cell populations (Pulendran, et al., $Science$ 337, 431-435 (2012); Tang, et al., $Immunol$ $Rev$ 249, 158-175 (2012)). However, the inability to identify helminth-associated PAMPs and corresponding receptors on mammalian immune cells suggest that type 2 immune responses are initiated by distinct molecular mechanisms (Pulendran, et al., *Science* 337, 431-435 (2012)). Herein it is shown that type 2-associated progenitor cell populations express elevated levels of carbonic anhydrase (Car) enzymes. Carbonic anhydrases are a family of clinically important metabolic enzymes that regulate pH and have been targeted to treat multiple disease states including glaucoma and gastric ulcers (Supuran, et al., *Nat Rev Drug Discov* 7, 168-181 (2008); Supuran, et al., *Medicinal Research Reviews* 23, 146-189 (2003)). Studies herein demonstrate that inhibition of Car enzyme activity was sufficient to prevent murine mast cell development from hematopoietic progenitor cells in vitro. Further, in vivo studies revealed that treatment of mice with an FDA-approved Car inhibitor was sufficient to prevent mast cell responses and type 2 cytokine-mediated inflammation in the context of anti-helminth immunity and food allergy-like disease. In contrast, Car inhibition promoted protective immunity to *Aspergillus fumigatus*, suggesting that Car enzymes can be targeted to selectively affect specific modules of the immune system. Finally, it is demonstrated that Car enzyme inhibition was sufficient to prevent human mast cell development from peripheral progenitor cells. These data suggest that Car enzymes activate in the context of infection- or allergen-induced metabolic alterations, initiate mast cell differentiation and the development of type 2 cytokine-mediated inflammation. Collectively, these studies identify a previously unappreciated enzymatic mechanism through which mammalian immune cells are instructed and provide insight into the therapeutic potential of FDA-approved Car inhibitors. Thus, as described herein, carbonic anhydrase enzymes may be targeted to, e.g., regulate mast cell responses, treat mastocytosis, treat allergic inflammation and treat parasite infections (e.g., helminth infections), as well as other diseases/conditions described herein.

As described herein, the present invention provides methods and compositions for treating an allergic disease, a bacterial infection, a fungal infection, a viral infection, mastocytosis or mast cell-mediated inflammation. In certain embodiments, the methods and compositions of the invention are not used to treat a fungal infection. In certain embodiments, the methods and compositions of the invention are not used to treat a viral infection. In certain embodiments, the methods and compositions of the invention are not used to treat a bacterial infection. Thus, the present invention provides methods and compositions for treating an allergic disease, mastocytosis or mast cell-mediated inflammation.

Methods of the Invention

Accordingly, the present invention provides methods for treating mast cell-mediated inflammation and allergic diseases, including asthma and food allergies. The method also provides the use of a Car enzyme inhibitor optionally in combination with administering one or more additional therapeutic agent(s), such as an anti-histamine, a steroid, immunotherapy (e.g., allergy shots, oral tolerance therapy, etc.), a decongestant, a bronchodilator, a mast cell stabilizer, a leukotriene modifier and/or an anti-IgE therapy (e.g., an anti-IgE therapeutic antibody) for treating allergic diseases. In certain embodiments, the Car enzyme inhibitor and the one or more additional therapeutic agent(s) produce a synergistic effect.

Thus, certain embodiments of the invention provide methods for treating allergic diseases comprising administering to a mammal (e.g., a patient) in need thereof an effective amount of a Car enzyme inhibitor.

The term "allergic disease" refers to a condition caused by hypersensitivity of the immune system in response to an environmental exposure. Examples of the allergic diseases that can be treated include, but are not limited to, asthma, atopic dermatitis, contact dermatitis, hay fever, allergic conjunctivitis, allergic rhinitis, anaphylaxis, eosinophilic esophagitis, food allergies, and mastocytosis (i.e., allergen-induced mastocytosis). Another example of an allergic disease is chronic itch (pruritus).

In another aspect, the invention provides methods for treating a bacterial infection comprising administering to a mammal (e.g., a patient) in need thereof an effective amount of a Car enzyme inhibitor.

Non-limiting examples of bacterial infections include, e.g., *Klebsiella pneumoniae* and *Pseudomonas aeruginosa*. In certain embodiments, the bacterial infection is a gram negative bacterial infection.

In another aspect, the invention provides methods for treating a fungal infection comprising administering to a mammal (e.g., a patient) in need thereof an effective amount of a Car enzyme inhibitor.

Non-limiting examples of fungal infections include infections caused by *Aspergillus fumigates*, or other *Aspergillus* species, as well as *Candida* species, *Cryptococcus* species, *Histoplasma capsulatum*, *Pneumocystis jirovecii*, and *Stachybotrys chartarum*.

In another aspect, the invention provides methods for treating a viral infection (e.g., HIV, Dengue, etc.) comprising administering to a mammal (e.g., a patient) in need thereof an effective amount of a Car enzyme inhibitor.

Non-limiting examples of viral infections include HIV and Dengue.

In another aspect, the invention provides methods for treating mastocytosis comprising administering to a mammal (e.g., a patient) in need thereof an effective amount of a Car enzyme inhibitor.

As used herein, the term "mastocytosis" refers to a disease characterized by the presence of too many mast cells in various organs and tissues, including but not limited to, helminth- or allergen-induced mastocytosis, Cutaneous Mastocytosis, Indolent Systemic Mastocytosis, Systemic Mastocytosis with associated Clonal Hematologic Non-Mast Cell Lineage Diseases (such as Myelodysplastic Syndrome, Myeloproliferative Syndrome, Acute myeloid leukemia, Non-Hodkin's Lymphoma), Aggressive Systemic Mastocytosis, Mast Cell Leukemia, Mast Cell Activation Syndrome, and Localized Mast Cell Proliferations (such as Mast Cell Sarcoma and Extracutaneous Mastocytoma).

In another aspect, the invention provides methods for treating mast cell-mediated inflammation comprising administering to a mammal (e.g., a patient) in need thereof an effective amount of a Car enzyme inhibitor.

As used herein, the term "mast cell-mediated inflammation" refers to any inflammatory response and/or pathology that is promoted or supported by mast cell development and/or activation. This includes mast cell responses promoted by exposure to allergens, infectious agents, or unknown stimuli. In certain embodiments, the mast cell-mediated inflammation is caused by mastocytosis, a parasite infection (e.g., a helminth parasite, such as *Trichinella spiralis* infection) or an allergy (e.g., a food allergy or food allergy-like disease). In certain embodiments, the mast cell-medicated inflammation is caused by mastocytosis or an allergy. In certain embodiments, the mast cell-mediated inflammation is mast cell-mediated intestinal inflammation.

In certain embodiments, the mast cell-mediated inflammation is mast cell-mediated airway inflammation (e.g., eosinophilic airway inflammation).

In another aspect, the invention provides methods for treating a parasite infection comprising administering to a mammal (e.g., a patient) in need thereof an effective amount of a Car enzyme activator. The method also provides the use of a Car enzyme activator optionally in combination with administering one or more additional therapeutic agent(s), such as an anti-parasitic (e.g., Benzimidazoles (Albendazole, Mebendazole, Thiabendazole, etc.), Abamectin, Diethylcarbamazine, Ivermectin, Suramin, Praziquantel, Spiroinodles, Pyrantel pamoate, Niclosamide, Nitazoxanide, Oxyclozanide, Octadepsipeptides, Aminoacetonitrile or Pelletierine sulphate).

As described herein, parasite infections include, but are not limited to, protozoa infections (e.g., *Leishmania major* infections, *Plasmodium* infections or Malaria) and helminth infections (e.g., an infection caused by a parasite belonging to one of the three major parasitic helminth families: nematodes, cestodes and trematodes).

Accordingly, in another aspect, the invention provides methods for treating helminth infections comprising administering to a mammal (e.g., a patient) in need thereof an effective amount of a Car enzyme activator. In certain embodiments, the helminth infection is a *Trichinella spiralis* infection. In certain embodiments, the helminth infection is a *Strongyloides* infection.

In another aspect, the invention provides methods for treating protozoa infections comprising administering to a mammal (e.g., a patient) in need thereof an effective amount of a Car enzyme activator. In certain embodiments, the protozoa infection is a *Leishmania major* infection, a *Plasmodium* infection or Malaria.

The methods of the invention may further comprise administering one or more additional therapeutic agent(s). Thus, in certain embodiments, the methods for treating allergic diseases, bacterial infections, fungal infections, viral infections, mastocytosis and/or mast cell-mediated inflammation may further comprise administering one or more additional therapeutic agent(s), such as an anti-histamine, a steroid, immunotherapy (e.g., an allergy shot, oral tolerance therapy, etc.), a decongestant, a bronchodilator, a mast cell stabilizer, a leukotriene modifier and/or an anti-IgE therapy (e.g., an anti-IgE therapeutic antibody). In certain embodiments, the methods for treating a parasite may further comprise administering one or more additional therapeutic agent(s), such as an anti-parasitic (e.g., Benzimidazoles (Albendazole, Mebendazole, Thiabendazole, etc.), Abamectin, Diethylcarbamazine, Ivermectin, Suramin, Praziquantel, Spiroinodles, Pyrantel pamoate, Niclosamide, Nitazoxanide, Oxyclozanide, Octadepsipeptides, Aminoacetonitrile, and Pelletierine sulphate).

In certain embodiments, the one or more additional therapeutic agent(s) is/are administered simultaneously or sequentially with the Car enzyme inhibitor/activator. In certain embodiments, the one or more additional therapeutic agent(s) is/are administered simultaneously with the Car enzyme inhibitor/activator. In certain embodiments, a pharmaceutical composition/formulation comprising the Car enzyme inhibitor/activator and the one or more additional therapeutic agent(s) is administered. In certain embodiments, the Car enzyme inhibitor/activator and the one or more additional therapeutic agent(s) are administered sequentially. In certain embodiments, the Car enzyme inhibitor/activator is administered first and the one or more additional therapeutic agent(s) is administered second. In certain embodiments the one or more additional therapeutic agent(s) is administered first and the Car enzyme inhibitor/activator is administered second.

The term "mammal" refers to any mammalian species such as a human, mouse, rat, dog, cat, hamster, guinea pig, rabbit, livestock, and the like. Accordingly, in certain embodiments, the mammal is a human, mouse, rat, dog, cat, hamster, guinea pig, rabbit or livestock. In certain embodiments, the mammal is a patient (e.g., a human patient). In certain embodiments, the mammal is a pet, such a dog, cat, hamster, guinea pig or rabbit. In certain embodiments, the mammal is a livestock mammal (e.g., a cow, sheep, horse, pig, chicken, etc.).

The terms "treat" and "treatment" refer to both therapeutic treatment and prophylactic or preventative measures, wherein the object is to prevent or decrease an undesired physiological change or disorder, such as a parasite infection, a bacterial infection, a fungal infection, a viral infection, mastocytosis, mast cell-mediated inflammation or an allergic disease. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

Formulations, Combinations and Kits of the Invention

In another aspect, the invention provides formulations (e.g., pharmaceutical formulations) that include a Car inhibitor one or more additional therapeutic agent(s). For example, in certain embodiments, the invention provides formulations (e.g., pharmaceutical formulations) that include a Car inhibitor and an anti-histamine; a Car inhibitor and an anti-IgE therapy, e.g., an anti-IgE therapeutic antibody, such as a monoclonal antibody; a Car inhibitor and a steroid; a Car inhibitor and a decongestant; a Car inhibitor and a bronchodilator; a Car inhibitor and a mast cell stabilizer; a Car inhibitor and a leukotriene modifier; or a Car inhibitor and an immunotherapy (e.g., an allergy shot, oral tolerance therapy, etc.).

Thus, in certain embodiments, the invention provides a formulation comprising a Car inhibitor and an anti-histamine. In certain embodiments, the invention provides a formulation comprising a Car inhibitor and an anti-IgE therapy. In certain embodiments, the invention provides a formulation comprising a Car inhibitor and a steroid. In certain embodiments, the invention provides a formulation comprising a Car inhibitor and an immunotherapy. In certain embodiments, the invention provides a formulation comprising a Car inhibitor and a decongestant. In certain embodiments, the invention provides a formulation comprising a Car inhibitor and a bronchodilator. In certain embodiments, the invention provides a formulation comprising a Car inhibitor and a mast cell stabilizer. In certain embodiments, the invention provides a formulation comprising a Car inhibitor and a leukotriene modifier. In certain embodiments, the formulation is a pharmaceutical formulation and further comprises a pharmaceutically acceptable carrier.

In another aspect, the invention provides a combination of a) a Car enzyme inhibitor; and b) one or more additional therapeutic agent(s), for the prophylactic or therapeutic treatment of an allergic disease, a bacterial infection, a fungal infection, a viral infection, mastocytosis or mast cell-mediated inflammation. In certain embodiments, the one or more additional therapeutic agent(s) is an anti-histamine, an anti-IgE therapy (e.g., an anti-IgE therapeutic antibody), a steroid, a decongestant, a bronchodilator, a mast cell stabilizer, a leukotriene modifier and/or an immunotherapy.

In another aspect, the invention provides a kit comprising a Car enzyme inhibitor, packaging material, and instructions for administering the Car enzyme inhibitor to a mammal (e.g., a patient) in need thereof to treat an allergic disease, a bacterial infection, a fungal infection, a viral infection, mastocytosis or mast cell-mediated inflammation. In certain embodiments, the kit further comprises one or more additional therapeutic agent(s). In certain embodiments, the one or more additional therapeutic agent(s) is an anti-histamine, an anti-IgE therapy (e.g., an anti-IgE therapeutic antibody), a steroid, a decongestant, a bronchodilator, a mast cell stabilizer, a leukotriene modifier and/or an immunotherapy.

In another aspect, the invention provides formulations (e.g., pharmaceutical formulations) that include a Car activator and one or more additional therapeutic agent(s). In certain embodiments, the one or more additional therapeutic agent(s) is an anti-parasitic (e.g., Benzimidazoles (Albendazole, Mebendazole, Thiabendazole, etc.), Abamectin, Diethylcarbamazine, Ivermectin, Suramin, Praziquantel, Spiroinodles, Pyrantel pamoate, Niclosamide, Nitazoxanide, Oxyclozanide, Octadepsipeptides, Aminoacetonitrile, and Pelletierine sulphate).

In another aspect, the invention provides a combination of a) a Car enzyme activator; and b) one or more additional therapeutic agent(s), for the prophylactic or therapeutic treatment of a parasite infection. In certain embodiments, the one or more additional therapeutic agent(s) is an anti-parasitic (e.g., Benzimidazoles (Albendazole, Mebendazole, Thiabendazole, etc.), Abamectin, Diethylcarbamazine, Ivermectin, Suramin, Praziquantel, Spiroinodles, Pyrantel pamoate, Niclosamide, Nitazoxanide, Oxyclozanide, Octadepsipeptides, Aminoacetonitrile, and Pelletierine sulphate).

In another aspect, the invention provides a kit comprising a Car enzyme activator, packaging material, and instructions for administering the Car enzyme activator to a mammal (e.g., a patient) in need thereof to treat a parasite infection (e.g., a helminth infection). In certain embodiments, the kit further comprises one or more additional therapeutic agent(s). In certain embodiments, the one or more additional therapeutic agent(s) is an anti-parasitic (e.g., Benzimidazoles (Albendazole, Mebendazole, Thiabendazole, etc.), Abamectin, Diethylcarbamazine, Ivermectin, Suramin, Praziquantel, Spiroinodles, Pyrantel pamoate, Niclosamide, Nitazoxanide, Oxyclozanide, Octadepsipeptides, Aminoacetonitrile, and Pelletierine sulphate).

Car Enzyme Inhibitors and Activators

As discussed herein, carbonic anhydrases (Car) are a family of metabolic enzymes that regulate pH and $CO_2$ homeostasis and have been targeted to treat a number of diseases, including glaucoma and gastric ulcers (Supuran, C. T. 2008. *Nat Rev Drug Discov* 7:168-181, which is hereby incorporated by reference herein). The Car enzymes found in mammals are divided into four broad subgroups, which, in turn consist of several isoforms: cytosolic Car (Car1, Car2, Car3, Car7, Car13), mitochondrial Car (Car5A, Car5B), secreted Car (Car6), and membrane-associated Car (Car4, Car9, Car12, Car14). Additionally, there are three additional "acatalytic" Car isoforms (Car8, Car10, Car11) whose functions remain unclear.

The term "Car inhibitor" as used herein includes any compound or treatment capable of inhibiting the expression and/or function of a carbonic anhydrase enzyme (Car) (e.g., inhibits transcription, RNA maturation, RNA translation, post-translational modification, or enzymatic activity). For example, in certain embodiments, the inhibitor detectably inhibits the expression level or biological activity of a Car as measured, e.g., using an assay described herein. In certain embodiments, the inhibitor inhibits the expression level or biological activity of a Car by at least about 5%, at least about 10%, at least about 20%, at least about 30%, at least about 40%, at least about 50%, at least about 60%, at least about 70%, at least about 80%, or at least about 90%.

The inhibitor may be of natural or synthetic origin. For example, it may be a nucleic acid, a polypeptide, a protein, a peptide, or an organic compound. In one embodiment, the inhibitor is a siRNA, shRNA, a small molecule or an antibody.

In certain embodiments, the inhibitor is an RNA interference molecule. For example, in certain embodiments, the inhibitor is an antisense nucleic acid (e.g., siRNA or shRNA) capable of inhibiting transcription of a Car or translation of the corresponding messenger RNA. An art worker can design an antisense nucleic acid using commercially available software and the gene sequence of a Car, which are known in the art.

In certain embodiments, the inhibitor involves the use of CRISPR/Cas9 to inhibit the expression of a Car (see, e.g., Example 1).

In certain embodiments, the inhibitor is a polypeptide, for example, an antibody against a Car, or a fragment or derivative thereof, such as a Fab fragment, a CDR region, or a single chain antibody.

The term "small molecule" includes organic molecules having a molecular weight of less than about 1000 amu. In one embodiment a small molecule can have a molecular weight of less than about 800 amu. In another embodiment a small molecule can have a molecular weight of less than about 500 amu.

For example, carbonic anhydrase inhibitors (Car enzyme inhibitors) include a class of pharmaceuticals that suppress the activity of carbonic anhydrase enzymes. Their clinical use has been established as antiglaucoma agents, diuretics, and antiepileptics, in the management of mountain sickness, gastric and duodenal ulcers, neurological disorders, or osteoporosis.

Non-limiting examples of Car enzyme inhibitors that may be used in the present invention include Methazolamide, Acetazolamide, Brinzolamide, Dichlorphenamide, Topiramate or Zonisamide. A specific Car enzyme inhibitor is Methazolamide. Other Car enzyme inhibitors are discussed in Talibov et al., Journal of Medicinal Chemistry, 2016, 59, 2083-2093, which is hereby incorporated by reference in its entirety. For example, Car enzyme inhibitors that may be used in the present invention also include the following compounds:

| 1 | 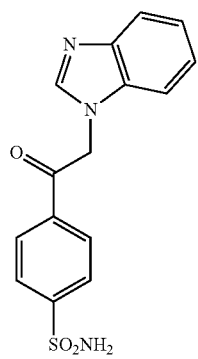 | 5 | 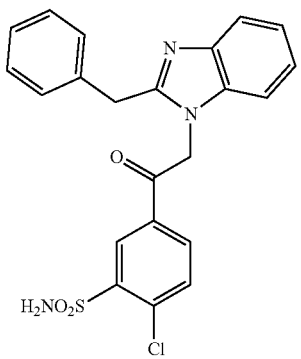 |
| 2 | 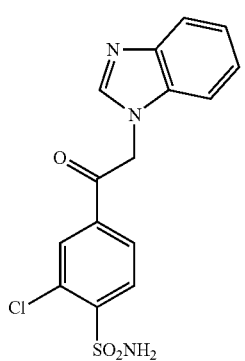 | 6 | 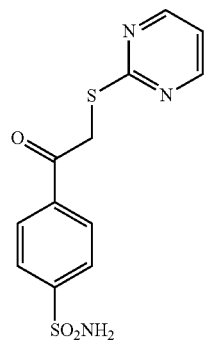 |
| 3 | 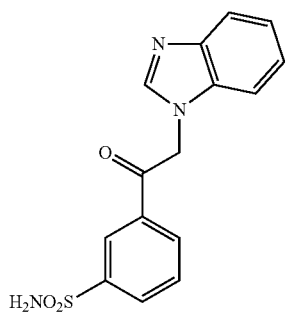 | 7 | 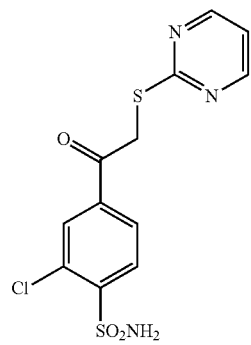 |
| 4 | 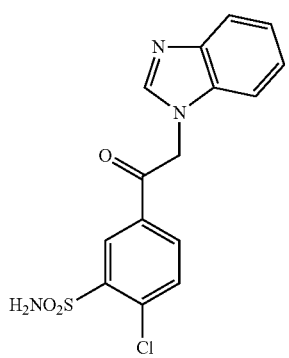 | 8 | 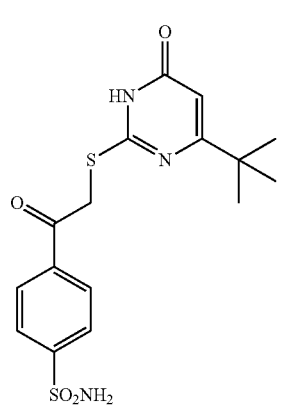 |

9
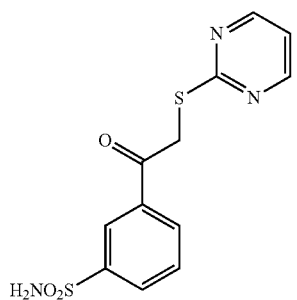

10
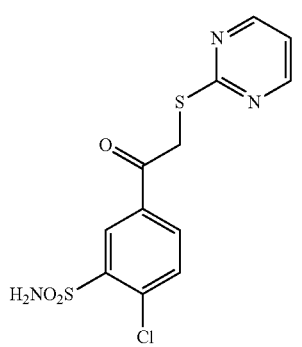

11
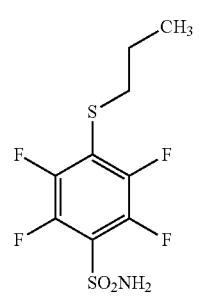

12
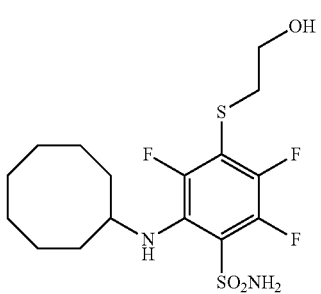

13
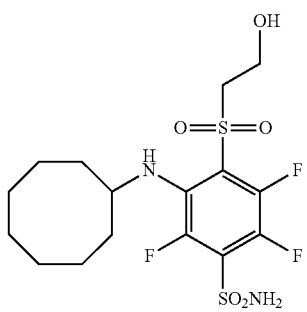

14
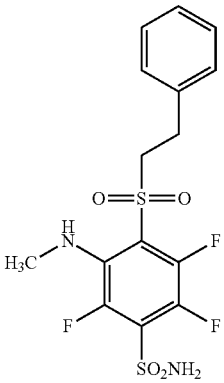

15
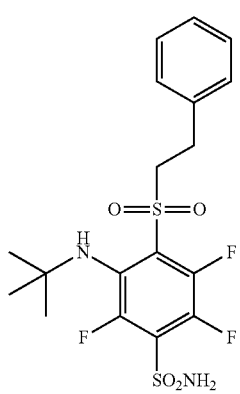

16
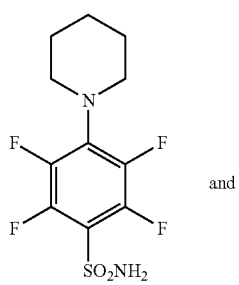

and

17
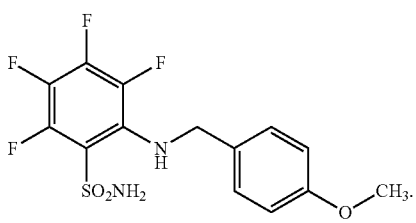

In certain embodiments, the inhibitor is a selective Car inhibitor. For example, the Car inhibitor may be at least 5, at least 10, at least 50, at least 100, at least 500, or at least 1,000 fold selective for a given Car (e.g., Car1, Car2, Car3, Car7, Car13, Car5A, Car5B, Car6, Car4, Car9, Car12, Car14, Car8, Car10 or Car11) over another Car in a selected assay (e.g., an assay described in the Examples herein). In certain embodiments, the inhibitor selectively inhibits Car1. In certain embodiments, the Car inhibitor is:

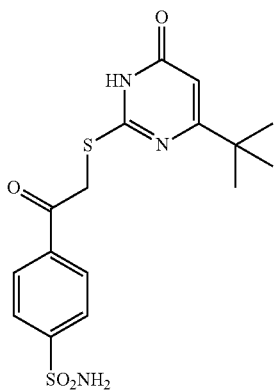

In certain embodiments, the Car inhibitor is:

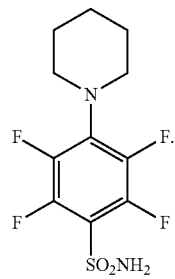

As used herein, the terms "carbonic anhydrase enzyme activator (Car enzyme activator)" includes any compound or treatment capable of enhancing the expression and/or function of a carbonic anhydrase enzyme (Car) (e.g., enhances transcription, RNA maturation, RNA translation, post-translational modification, or enzymatic activity (e.g., enhances activation of the enzyme)). For example, in certain embodiments, the activator detectably enhances the expression level or enzymatic activity of a Car enzyme as measured, e.g., using an assay described herein. In certain embodiments, the activator enhances the expression level or enzymatic activity of a Car enzyme by at least about 5%, at least about 10%, at least about 20%, at least about 30%, at least about 40%, at least about 50%, at least about 60%, at least about 70%, at least about 80%, or at least about 90%.

The activator may be of natural or synthetic origin. For example, it may be a polypeptide, a protein, a peptide, or small molecule (e.g., an organic compound).

The term "small molecule" includes organic molecules having a molecular weight of less than about 1000 amu. In one embodiment a small molecule can have a molecular weight of less than about 800 amu. In another embodiment a small molecule can have a molecular weight of less than about 500 amu.

Non-limiting examples of Car enzyme activators that may be used in the present invention include phenylalanine, histamine, serotonin, catecholamine, adrenaline, beta-alanyl-histidine, dopamine, and tryptophan.

In certain embodiments, the activator is a selective Car activator. For example, the Car activator may be at least 5, at least 10, at least 50, at least 100, at least 500, or at least 1,000 fold selective for a given Car (e.g., Car1, Car2, Car3, Car7, Car13, Car5A, Car5B, Car6, Car4, Car9, Car12, Car14, Car8, Car10 or Car11) over another Car in a selected assay (e.g., an assay described in the Examples herein).

Additional Therapeutic Agents

As described herein, the methods of the invention may further comprise administering one or more additional therapeutic agent(s). In certain embodiments, the one or more additional therapeutic agent(s), is an anti-histamine, a steroid, immunotherapy (e.g., an allergy shot, oral tolerance therapy, etc.), a decongestant, a bronchodilator, a mast cell stabilizer, a leukotriene modifier and/or an anti-IgE therapy (e.g., an anti-IgE therapeutic antibody). In certain embodiments, the one or more additional therapeutic agent(s) is an anti-histamine. In certain embodiments, the one or more additional therapeutic agent(s) a steroid. In certain embodiments, the one or more additional therapeutic agent(s) immunotherapy (e.g., an allergy shot, oral tolerance therapy, etc.). In certain embodiments, the one or more additional therapeutic agent(s) is a decongestant. In certain embodiments, the one or more additional therapeutic agent(s) is a bronchodilator. In certain embodiments, the one or more additional therapeutic agent(s) is a mast cell stabilizer. In certain embodiments, the one or more additional therapeutic agent(s) is a leukotriene modifier. In certain embodiments, the one or more additional therapeutic agent(s) an anti-IgE therapy (e.g., an anti-IgE therapeutic antibody, such as a monoclonal antibody (e.g., Omalizumab (Xolair)). In certain embodiments, the one or more additional therapeutic agent(s) is an anti-parasitic.

A histamine antagonist, commonly called an antihistamine, is a pharmaceutical drug class that includes two types of drugs: histamine $H_1$-receptor antagonists and histamine $H_2$-receptor antagonists. Antagonists of the histamine $H_1$-receptor are used to treat allergic reactions in the nose (e.g., itching, runny nose, and sneezing) and which are used off-label for insomnia. They are sometimes also used to treat motion sickness or vertigo caused by problems with the inner ear. Antagonists of the histamine $H_2$-receptor are used to treat gastric acid conditions (e.g., peptic ulcers and acid reflux). They work by binding to histamine $H_1$ receptors in mast cells, smooth muscle, and endothelium in the body and tuberomammillary nucleus the brain or histamine $H_2$ receptors in the upper gastrointestinal tract, primarily in the stomach.

Non-limiting examples of antihistamines that may be used in the present invention include: Acrivastine, Azelastine, Bilastine, Brompheniramine, Buclizine, Bromodiphenydramine, Carbinoxamine, Cetirizine (Zyrtec; metabolite of hydroxyzine, its prodrug), Chlorpromazine, Cimetidine, Cyclizine, Chlorphenamine, Chlorodiphenhydramine, Clemastine, Cyproheptadine, Desloratadine, Dexbrompheniramine, Dexchlorpheniramine, Dimetindene, Diphenhydramine (Benadryl), Ebastine, Embramine, Famotidine, Fexofenadine (Allegra), Hydroxyzine (Vistaril), Lafutidine, Levocetirizine, Loratadine (Claritin), Nizatidine, Olopatadine, Phenindamine, Pheniramine, Phenyltoloxamine, Promethazine, Pyrilamine, Ranitidine, Roxatidine, Rupatadine, Tiotidine, Tripelennamine, and Triprolidine.

Anti-IgE therapies that may be used in the present invention include anti-IgE therapeutic antibodies, such as a monoclonal antibody. A non-limiting example of a suitable monoclonal antibody is Omalizumab (Xolair).

A steroid is an organic compound, typically containing four rings arranged in a specific configuration. Steroids have two principal biological functions: certain steroids (such as cholesterol) are important components of cell membranes which alter membrane fluidity, and many steroids are signaling molecules which activate steroid hormone receptors.

Generally, the steroid core structure is composed of seventeen carbon atoms, bonded in four "fused" rings: three six-member cyclohexane rings (rings A, B and C in the first illustration) and one five-member cyclopentane ring (the D ring). Steroids vary by the functional groups attached to this four-ring core and by the oxidation state of the rings. Sterols are forms of steroids with a hydroxyl group at position three and a skeleton derived from cholestane. Steroids can also vary more markedly by changes to the ring structure (for example, ring scissions which produce secosteroids, such as vitamin $D_3$).

Non-limiting examples of steroids that may be used in the present invention include: beclomethasone, ciclesonide, fluticasone proprionate, fluticasone furoate, mometasone, budesonide, triamcinolone, dexamethasone, deltasone, and prednisone.

Immunotherapy is the treatment of a disease or condition by inducing, enhancing, or suppressing an immune response. Immunotherapies that are designed to elicit or amplify an immune response are classified as activation immunotherapies, while immunotherapies that reduce or suppress are classified as suppression immunotherapies.

Non-limiting examples of immunotherapies that may be used in the present invention include, allergy shots and oral tolerance therapies.

Decongestants are a type of agent that is used to relieve nasal congestion in the upper respiratory tract. Non-limiting examples of decongestants that may be used in the present invention include pseudophedrine, phenylephrine, and oxymetazoline.

Bronchodilators are a type of agent that dilates the bronchi and bronchioles, decreasing resistance in the respiratory airway and increasing airflow to the lungs. Non-limiting examples of bronchodilators that may be used in the present invention include albuterol and levalbuterol.

Mast cell stabilizers are generally cromone medications that are used to prevent or control certain allergic disorders. They block a calcium channel essential for mast cell degranulation, stabilizing the cell and thereby preventing the release of histamine and related mediators. Non-limiting examples of mast cell stabilizers that may be used in the present invention include cromolyn sodium, lodoxamide, and nedocromil.

Leukotriene modifiers are a type of agent that functions as a leukotriene-related enzyme inhibitor (arachidonate 5-lipoxygenase) or leukotriene receptor antagonist (cysteinyl leukotriene receptors) and consequently opposes the function of these inflammatory mediators. Non-limiting examples of leukotriene modifiers that may be used in the present invention include montelukast, zafirlukast, and zyflo.

Anti-parasitics are a class of medications which are indicated for the treatment of parasitic diseases. Non-limiting examples of anti-parasitics that may be used in the present invention include: Benzimidazoles (Albendazole, Mebendazole, Thiabendazole, etc.), Abamectin, Diethylcarbamazine, Ivermectin, Suramin, Praziquantel, Spiroinodles, Pyrantel pamoate, Niclosamide, Nitazoxanide, Oxyclozanide, Octadepsipeptides, Aminoacetonitrile, and Pelletierine sulphate.

Administration

Car enzyme inhibitors and activators can be formulated as pharmaceutical compositions and administered to a mammalian host, such as a human patient or other mammal, in a variety of forms adapted to the chosen route of administration, i.e., orally or parenterally, by intravenous, intramuscular, topical, sub-lingual, optical (e.g., eye drops), nasal (i.e., nasal spray) or subcutaneous routes. In certain embodiments, the Car enzyme inhibitors and activators may be delivered via delayed administration.

Thus, Car enzyme inhibitors and activators may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, a Car enzyme inhibitor or activator may be applied in pure form, i.e., when they are liquids. However, it will generally be desirable to administer them to the skin as compositions or formulations, in combination with a dermatologically acceptable carrier, which may be a solid or a liquid. In certain embodiments, a Car enzyme inhibitor or activator may be delivered using a patch.

Useful solid carriers include finely divided solids such as talc, clay, microcrystalline cellulose, silica, alumina and the like. Useful liquid carriers include water, alcohols or glycols or water-alcohol/glycol blends, in which a Car enzyme inhibitor or activator can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver a Car enzyme inhibitor or activator to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of Car enzyme inhibitors and activators can be determined by comparing their in vitro activity, and in vivo activity in animal models. Methods for the extrapolation of effective dosages in mice, and other animals, to humans are known to the art; for example, see U.S. Pat. No. 4,938,949.

The amount of a Car enzyme inhibitor or activator, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

A Car enzyme inhibitor or activator may be conveniently formulated in unit dosage form; for example, containing 5 to 1000 mg, conveniently 10 to 750 mg, most conveniently, 50 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

As discussed herein, Car enzyme inhibitors or activators can also be administered in combination with other therapeutic agents, for example, other agents that are useful for the treatment of a parasite infection, an allergic disease, a bacterial infection, a fungal infection, a viral infection, mastocytosis or mast cell-mediated inflammation. Examples of such agents include antihistamines, anti-IgE therapies, steroids, immunotherapies, decongestants, bronchodilators, mast cell stabilizers, leukotriene modifiers, as well as anti-parasitics. Accordingly, one embodiment the invention also provides a composition comprising a Car enzyme inhibitor or activator, or a pharmaceutically acceptable salt thereof, at least one other therapeutic agent, and a pharmaceutically acceptable diluent or carrier. The invention also provides a kit comprising a Car enzyme inhibitor or activator, or a pharmaceutically acceptable salt thereof, at least one other therapeutic agent, packaging material, and instructions for administering the Car enzyme inhibitor or activator, or the pharmaceutically acceptable salt thereof, and the other therapeutic agent or agents to a mammal in need thereof to treat a parasite infection, an allergic disease, a bacterial infection, a fungal infection, a viral infection, mastocytosis or mast cell-mediated inflammation.

The invention will now be illustrated by the following non-limiting Examples.

EXAMPLES

Example 1. Carbonic Anhydrase Enzymes Regulate Mast Cell-Mediated Inflammation Car enzyme inhibition prevents mast cell responses and inflammation following *Trichinella spiralis* infection or the induction of food allergy-like disease.

Abstract

Type 2 cytokine responses are necessary for the development of protective immunity to helminth parasites but also cause the inflammation associated with allergies and asthma. Recent studies have found that peripheral hematopoietic progenitor cells contribute to type 2 cytokine-mediated inflammation through their enhanced ability to develop into mast cells. Here it is shown that carbonic anhydrase (Car) enzymes are upregulated in type 2-associated progenitor cells and it is demonstrated that Car enzyme inhibition is sufficient to prevent murine mast cell responses and inflammation following *Trichinella spiralis* infection or the induction of food allergy-like disease. Further, CRISPR/Cas9 technology was employed and it was illustrated that genetically editing Car1 is sufficient to selectively reduce mast cell development. Finally, it was demonstrated that Car enzymes can be targeted to prevent human mast cell development. Collectively these studies identify a previously unrecognized role for Car enzymes in regulating mast cell lineage commitment and suggest that Car enzyme inhibitors may possess therapeutic potential that can be employed to treat mast cell-mediated inflammation.

Introduction

Type 2 cytokine responses are characterized by the development of T helper type 2 ($T_H2$) cells, interleukin (IL)-4, -5, -9 and -13 expression, basophil and mast cell responses and increased IgE production. Type 2 cytokines are necessary for the development of protective immunity to helminth parasites but also promote the pathology associated with allergies and asthma (Allen, et al., 2011. *Nat Rev Immunol* 11:375-388; Pulendran, et al., 2012. *Science* 337:431-435). Helminth parasites infect an estimated 2 billion people and cause anemia, retarded growth, and exert enormous economic burdens on heavily infected areas (Allen, et al., 2011. *Nat Rev Immunol* 11:375-388). Allergic diseases, including food allergies, have risen to epidemic proportions in developed areas of the world and result in significant morbidity and even death (Pulendran, et al., 2012. *Science* 337:431-435). Current therapeutic strategies to treat helminth infections and allergic inflammation are limited by an incomplete understanding of the events that promote type 2 inflammation (Pulendran, et al., 2012. *Science* 337:431-435).

An emerging body of literature has identified that type 2 inflammation can be promoted by specialized progenitor cells that enter peripheral tissues and undergo in situ hematopoiesis. These studies demonstrate that lineage negative, $CD34^+$, $c-Kit^+$ hematopoietic progenitors accumulate in peripheral tissues following stimulation with cytokine alarmins, exposure to helminths or the initiation of allergic inflammation (Saenz, et al., 2010. *Nature* 464:1362-1366; Siracusa, et al., 2013. *Immunity* 39:1158-1170). The conserved presence of these progenitors in the context of type 2 responses allow them to be characterized as type 2-associated. It has been shown that type 2 progenitors promote inflammation via their enhanced ability to develop into mast cells compared to phenotypically similar bone marrow (BM)-resident progenitors (Siracusa, et al., 2013. *Immunity* 39:1158-1170). Collectively, these studies suggest that targeting progenitors to prevent mast cell differentiation may be sufficient to regulate type 2 inflammation.

Here it is shown that type 2 progenitors express elevated levels of carbonic anhydrase (Car) enzymes. Carbonic anhydrases are a family of metabolic enzymes that regulate pH and $CO_2$ homeostasis and have been targeted to treat diseases including glaucoma and gastric ulcers (Supuran, C. T. 2008. *Nat Rev Drug Discov* 7:168-181). Car enzymes have also been associated with type 2 cytokine responses (Kamsteeg, et al., 2007. *J Invest Dermatol* 127:1786-1789; Wen, et al., 2014. *Journal of immunology* (Baltimore, Md.: 1950) 192:5481-5489). The studies described herein demonstrate that pan inhibition of Car enzymes with an FDA-approved inhibitor was sufficient to prevent inflammatory mast cell responses in the context of helminth infection and models of allergic inflammation. In contrast, Car enzyme inhibition promoted immunity to *Aspergillus fumigatus*, suggesting that Car enzymes can selectively affect specific immune modules. Further, selectively editing Car1 via CRISPR/Cas9 was sufficient to reduce mast cells development from stem cells but had no effect on macrophage commitment. Finally, it was demonstrated that Car enzyme inhibition was also sufficient to prevent human mast cell development. Collectively, these studies identify a previously unappreciated mechanism through which mammalian immune cells are instructed by inflammatory cues and provide insight into the therapeutic potential of targeting Car1 to treat mast cell-mediated inflammation.

Results

Mast Cells Express Elevated Levels of Carbonic Anhydrase Enzymes

First, the transcriptional profiles of naïve BM-resident progenitors were compared to those of type 2 progenitors (Siracusa, et al., 2013. *Immunity* 39:1158-1170) to identify fundamental pathways associated with mast cell development. The top 200 genes expressed at higher levels in type 2 progenitors were run through pathway analysis (Dennis, et al., 2003. *Genome Biol* 4:P3). Type 2 progenitors were enriched for genes associated with immune and defense responses, hematopoietic lineages, responses to wounding, and asthma (FIG. 1A). Type 2 progenitors also expressed genes associated with serine hydrolases, known to be present in mast cells (Long, et al., 2011. *Chem Rev* 111:6022-6063), and carbon-oxygen lyase activity (FIG. 1B). The carbon-oxygen lyase pathway was comprised of the genes encoding Car enzymes 1 and 2. To confirm these data, *Trichinella spiralis* (T.s)-induced progenitors were sort-purified from infected mice (Siracusa, et al., 2013. *Immunity* 39:1158-1170) and Car1 and 2 expression was compared to that of naïve BM progenitors. The genes encoding Car1 and 2 were expressed at significantly higher levels in T.s.-induced progenitors (FIG. 1C). Collectively, these data demonstrate that Car1 and 2 are highly expressed in mast cell precursors. Next, BM-derived basophils (Baso) and mast cells (MC), CD8 T cells (CD8), CD4 T cells (CD4), B cells, macrophages (Mac), and monocytes (Mono) were sort-purified and their expression levels of Car1 and 2 were evaluated. Car1 and 2 were expressed at significantly higher levels in mature mast cells compared to other populations (FIG. 1D). These data provoke the hypothesis that Car1 and 2 may regulate mast cell development.

Carbonic Anhydrase Enzyme Inhibitors Prevent In Vitro Mast Cell Development.

The Car enzyme inhibitor methazolamide (MZ) has been shown to inhibit Car1 and 2 (Supuran, C. T. 2008. *Nat Rev Drug Discov* 7:168-181). Therefore, mast cell developmental assays were employed (Saenz, et al., 2010. *Nature* 464:1362-1366; Siracusa, et al., 2011. *Nature* 477:229-233; Siracusa, et al., 2013. *Immunity* 39:1158-1170) to determine whether Car enzyme inhibition affected mast cell development. Importantly, cultures treated with MZ exhibited significantly reduced mast cell populations compared to controls (FIG. 1E). In addition to mast cells, type 2 progenitors are also capable of developing into basophils (Siracusa, et al., 2013. *Immunity* 39:1158-1170). Therefore, whether Car enzyme inhibition altered basophil development was sought to be determined. While treatment of cultures with MZ resulted in significantly increased percentages of basophils (FIG. 1F), Car enzyme inhibition resulted in decreased basophil numbers. Next, it was sought to be determined if Car enzyme inhibition alters the development of other myeloid cell populations (Marim, et al., 2010. *PLoS One* 5:e15263). Importantly, treatment with MZ had no effect on macrophage development (FIG. 1G).

Inhibition of Carbonic Anhydrase Enzymes is Sufficient to Prevent Infection-Induced Mastocytosis.

Protective immunity to *T. spiralis* is dependent on type 2 cytokine responses and is associated with the population expansion of mast cells and basophils (Giacomin, et al., 2012. *Journal of immunology* (Baltimore, Md.: 1950) 189: 4371-4378; Urban, et al., 2000. *J Immunol* 164:2046-2052). Therefore, *T. spiralis*-infected mice were treated with vehicle (Veh) or MZ, and mast cells and basophils were monitored. *Trichinella* infection resulted in increased percentages and numbers of mast cells in the mesenteric lymph nodes (mLNs) (FIG. 2A-2B), increased serum levels of mast cell protease 1 (Mcpt1) (FIG. 2C), increased expression of intestinal mcpt1 (FIG. 2D) and increased intestinal mast cells identified by histological analysis (FIG. 2E). Importantly, treatment of mice with MZ resulted in significantly reduced mast cell responses across these parameters (FIGS. 2A-2E), In contrast to mast cells, treatment of *Trichinella*-infected mice with MZ had no effect on infection-induced basophilia (FIGS. 2F-2G). These studies suggest that the moderate effects of Car enzyme inhibition on in vitro basophil development (FIG. 1F) may be a result of its actions on a limited pool of common progenitor shared between basophils and mast cells (Voehringer, D. 2013. *Nat Rev Immunol* 13:362-375).

Mast cells have been shown to play critical roles in the development of protective immunity to *T. spiralis* (Urban, et al., 2000. *J Immunol* 164:2046-2052; Voehringer, D. 2013. *Nat Rev Immunol* 13:362-375). Therefore, it was sought to be determined if the inhibition of *Trichinella*-induced mast cell responses correlated with reduced inflammation and immunity. As expected (Urban, et al., 2000. *J Immunol* 164:2046-2052), *Trichinella*-infected mice exhibited increased levels of IL-4, IL-5 and IL-13 production from mLN cells (FIG. 3A), increased intestinal expression of il4, il9, arg1 and retnla (FIG. 3B) and elevated serum levels of IgE (FIG. 3C). Importantly, *Trichinella*-infected mice treated with MZ exhibited significantly reduced type 2 responses as measured by these parameters (FIG. 3A-C). Moreover, significantly more worms were recovered from the intestines of mice treated with MZ (FIG. 3D). These data demonstrate that Car enzyme-mediated inhibition of mast cell responses is associated with reduced inflammation and a loss of protective immunity.

The ability of MZ to regulate inflammation could be a result of its effects on mast cells, lymphocytes or global immunosuppressive qualities. Therefore, a model of atopic dermatitis (AD)-like disease was first employed, in which type 2 cytokine responses and pathology are dependent on group 2 innate lymphoid cells (TLC2) and basophils (Kim, et al., 2013. *Sci Transl Med* 5:170ra116; Kim, et al., 2014. *Journal of immunology* (Baltimore, Md.: 1950) 193:3717-3725). Importantly, mice treated with MC903 in the presence of MZ exhibited equivalent or significantly increased type 2 cytokine production and similar AD-like pathology as controls (FIG. 3E-F). These data demonstrate that Car enzyme inhibition does not result in reduced ILC2- and basophil-dependent type 2 cytokine responses.

Mast cells are reported to operate as initiators of *Trichinella*-induced $T_H2$ cell development (Knight, et al., 2000. *J Exp Med* 192:1849-1856; Urban, et al., 2000. *J Immunol* 164:2046-2052), but are also supported by T cell activation (Voehringer, D. 2013. *Nat Rev Immunol* 13:362-375). Therefore, recombination-activating gene (Rag)1-deficient mice were treated with IL-3-anti-IL-3 complexes (IL-3C) and intestinal mast cell responses and peripheral basophilia were monitored (Finkelman, et al., 1993. *Journal of immunology* (Baltimore, Md.: 1950) 151:1235-1244; Ohmori, et al., 2009. *Journal of immunology* (Baltimore, Md.: 1950) 182:2835-2841). MZ treatment resulted in significantly reduced mast cell responses but had no effect on IL-3C-induced basophilia in Rag-deficient animals (FIG. 3G). These data demonstrate that Car enzyme inhibition is sufficient to selectively inhibit mast cell responses in lymphocyte-sufficient and -deficient environments.

Next it was sought to be determined if Car enzyme inhibition promotes immunosuppressive qualities. *Aspergillus fumigatus* is an opportunistic pathogen that thrives in immunosuppressed hosts (Espinosa, et al., 2014. *PLoS Pathog* 10:e1003940). Infecting mice with fluorescent *Aspergillus* reporter (FLARE) conidia (Espinosa, et al., 2014. *PLoS Pathog* 10:e1003940), allows live and dead spores to be identified in vivo. Neutrophil responses and fungal clearance were increased in MZ-treated mice (FIGS. 3H-3J). Collectively, these data demonstrate that Car enzyme inhibition does not promote broad immunosuppressive effects, but rather enhances anti-fungal immunity.

Figures 4A, 4B, 4C:
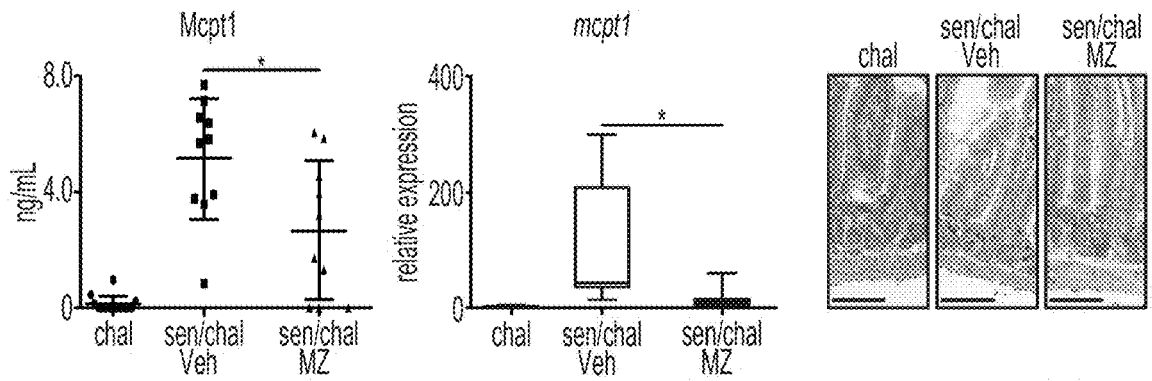
Figures 4D, 4E, 4F:
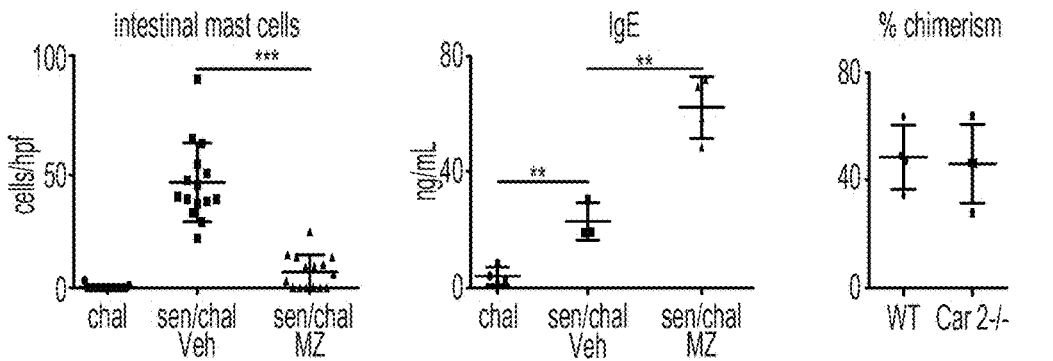

Inhibition of Carbonic Anhydrase Enzymes is Sufficient to Prevent Food Allergy-Induced Mast Cell Responses Food allergies are a significant and growing public health concern (Sicherer, et al., 2014. *J Allergy Clin Immunol* 133:291-307; quiz 308). Mast cells are critically important to the development of intestinal inflammation following sensitization and challenge with food antigens (Wang, et al., 2010. *J Allergy Clin Immunol* 126:306-316, 316 e301-312). Therefore, a model of food allergy-like disease was employed that promotes intestinal mastocytosis (Noti, et al., 2014. *J Allergy Clin Immunol* 133:1390-1399, 1399 e1391-1396) and mice were treated with Veh or MZ. Mice sensitized (sens) and challenged (chal) with chicken ovalbumin, a food allergen found in eggs (Dang, et al., 2014. *Pediatr Allergy Immunol* 25:639-643), exhibited increased serum levels of Mcpt1 (FIG. 4A), elevated intestinal expression of mcpt1 (FIG. 4B), increased intestinal mast cells identified by histological analysis (FIGS. 4C-4D), and increased serum levels of IgE (FIG. 4E). MZ-treated mice exhibited significantly decreased mast cell responses across all of these parameters (FIG. 4A-D), but had significantly increased IgE levels (FIG. 4E). Collectively, these studies demonstrate that pharmacologic inhibition of Car enzymes is sufficient to significantly reduce food allergy-induced mast cell responses. Further, the increased levels of IgE observed in MZ-treated mice suggest this treatment is not inhibiting lymphocyte activation. The increases observed are likely a result of reductions in mast cell populations capable of binding soluble IgE.

Carbonic Anhydrase 1 Positively Regulates Mast Cell Development.

Figures 4G, 4H, 4I:
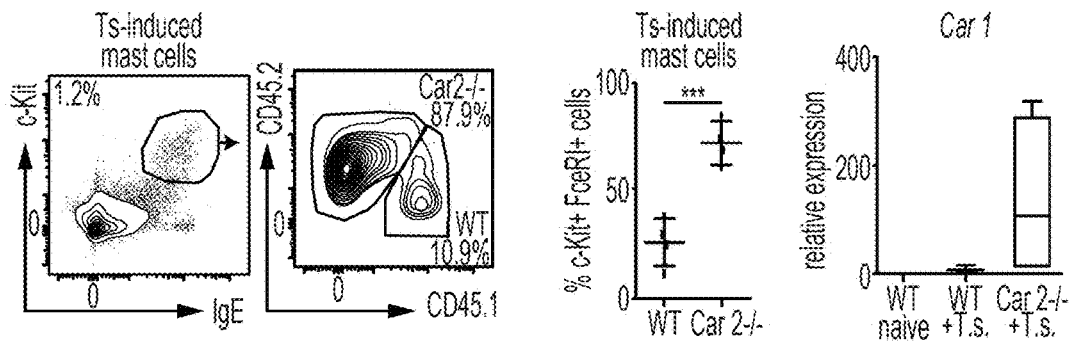

The experiments described herein show that inhibition of Car enzyme family members via a pan inhibitor is sufficient to prevent helminth- or allergen-induced mastocytosis. However, whether specifically targeting Car1 or 2 is sufficient to regulate mast cell responses remains unknown. To address this, mice were lethality irradiated and then were reconstituted with BM cells from wild type (WT) and Car2$^{-/-}$ mice at a 50/50 ratio. Both WT and Car2$^{-/-}$ cells were present at equal percentages (FIG. 4F); however, when chimeric mice were infected with *T. spiralis*, ~80% of *Trichinella*-induced mast cells were derived from Car2$^{-/-}$ cells (FIGS. 4G-4H). These data countered the working hypothesis that Car1 and 2 promote mast cell development. It has previously been shown that deletion of one Car enzyme can result in the increased expression of other family members (Pan, et al., 2006. *J Physiol* 571:319-327). Interestingly, it was found that chimeric mice reconstituted with 100% Car2$^{-/-}$ cells expressed higher levels of Car1 following *T. spiralis* infection than mice reconstituted with WT BM (FIG. 4I). Collectively, these data provoke the hypothesis that Car1 operates as a positive regulator of mast cell development.

Since Car1-deficient mice are not readily available, CRISPR/Cas9 technology was employed to genetically edit Car1 in murine embryonic stem cells. Car1 was edited in ~60% of embryonic stem cells electroporated with Car1-specific RNA guides and Cas9 protein (data not shown).

Further, when Car1-edited stem cells were cultured they exhibited a reduced capacity to develop into mast cells compared to controls (FIG. 4J) but showed no defect in macrophage development (FIG. 4K). Collectively, these studies illustrate that CRISPR/Cas9-mediated editing of Car1 results in a selective reduction in mast cell hematopoietic potential. However, whether Car1 regulates mast cell development via its effects on other Car family members requires further examination.

Carbonic Anhydrase Enzyme Inhibition is Sufficient to Prevent Human Mast Cell Development.

Patients suffering from allergic diseases such as food allergies present with increased mast cell responses, suggesting that targeting mast cell development may represent a viable therapeutic strategy (Bischoff, et al., 2005. *Gastroenterology* 128:1089-1113; Ramsay, et al., 2010. *Gastroenterol Hepatol* (NY) 6:772-777; Reimann, et al., 1988. *Am J Gastroenterol* 83:1212-1219; Voehringer, D. 2013. *Nat Rev Immunol* 13:362-375). As described herein, it has been identified that murine Car1 operates as a positive regulator of mast cell development. However, whether Car enzymes can be targeted to prevent human mast cell development remains unknown. Therefore, $CD34^+$ progenitor cells were isolated from the blood of healthy human donors and an established protocol was employed to grow human mast cells (Saito, et al., 2006. *Nat Protoc* 1:2178-2183). Human cultures treated with MZ exhibited significantly reduced percentages and total numbers of mast cells (FIGS. 4L-4M). The ability of MZ to prevent human mast cell development was found to be consistent across 5 individual donors (FIG. 4N).

Recent studies have begun to introduce a model through which alterations in metabolic processes can instruct immune cell development and activation (Pearce, et al., 2013. *Immunity* 38:633-643). Variations in pH often accompany infectious and inflammatory insults and can have potent effects on immune cell function (Lardner, A. 2001. *J Leukoc Biol* 69:522-530). The studies presented here suggest that, similar to germ-line encoded receptors that recognize pathogen-derived molecules (Tang, et al., 2012. *Immunol Rev* 249:158-175), Car enzymes may operate as sensory mechanisms that instruct immune cell hematopoiesis under inflammatory conditions. This hypothesis is supported by a recent study identifying Car4 as the signature gene expressed by pulmonary macrophages (Lavin, et al., 2014. *Cell* 159:1312-1326). The data presented herein suggest that Car1 operates as a positive regulator of mast cell development and that targeting Car1 may prove to be effective in treating mast cell-mediated inflammation.

Methods

Mice

C57BL(6) wild type (WT) mice were purchased from The Jackson Laboratory. Mice were maintained in specific pathogen-free facilities at the Rutgers New Jersey Medical School. All protocols were approved by the Rutgers Institutional Animal Care and Use Committee (IACUC). Car2-deficient mice on a C57BL(6) background were kindly provided by Dr. Manoocher Soleimani, University of Cincinnati.

Flow Cytometry and Cell Sorting

Cells were stained with monoclonal anti-mouse fluorescently conjugated antibodies: Sca-1 (D7), c-Kit (ACK2), CD3 (145-2C11), CD4 (GK1.5), CD8 (SK1), CD5 (53-73), CD19 (1D3), NK1.1 (PK136), CD11b (MI/70), CD11c (N418), CD16(32) (93), IgE (23G3), FcεRI (MAR-1), CD49b (DX5), CD115 (AFS98), F4/80 (BM8) and CD34 (RAM34) from eBioscience; or monoclonal anti-human fluorescently conjugated antibodies: CD19 (HIB19), FcεRI (AER-37), CD34 (4H11), c-Kit (104D2), TCRαβ (IP26) from eBioscience. Samples were acquired on a LSRII or LSRFORTESSA X-20 flow cytometer (BD Biosciences) and analyzed using FlowJo software (v10.0.5, Tree Star). Cell sorting was performed using a FACSAriaII (BD Bioscience). BM-resident and splenic progenitors were sort-purified as $CD3^-$, $CD19^-$, $CD11b^-$, $CD11c^-$, $NK1.1^-$, $Sca-1^-$, $FcεRI^-$, $CD34^+$, $c-Kit^+$ cells. Splenic progenitors were isolated on day 7-post *T. spiralis* infection.

Microarray and Gene Expression Analysis

Genome-wide transcriptional profiles were downloaded from the NCBI Gene Expression Omnibus (GEO) under the Query DataSet GSE52485. The Affymetrix CEL files from BM progenitor data sets (GSM1267747, GSM1267748, GSM1267749) and type 2 progenitor data sets (GSM1267744, GSM1267745, GSM1267746) were loaded into Partek® Genomics Suite® software, version 6.6 Copyright©; 2014 Partek Inc., St. Louis, MO, USA. The CEL files were RMA normalized and a 1-way ANOVA analysis was performed. A subset of the top 200 annotated genes which were up-regulated in type 2 progenitors vs BM progenitors and passed a p-value cut-off of 0.05 or less was then merged with the RMA normalized signal intensities and exported as a text file. The top 200 enriched genes in type 2 progenitors were analyzed for gene pathways with DAVID (david.abcc.ncifcrf.gov).

Isolation & Processing of Immune Cells for Car Expression Profiling

Indicated cell populations were isolated from 4 naïve CCR2-GFP mice on a C57BL(6) background. B cells and T cells were sorted from spleens. B cells were sorted-purified as $CD45^+$ $CD11c^-NK1.1^-CCR2GFP^-B220^+$. T cells were sort-purified as $CD45^+CD11c^-NK1.1^-CCR2-GFP^-B220^-$ $Thy1.2^+$ and either $CD4^+$ or $CD8^+$. Macrophages and monocytes were isolated from collagenase-digested lungs. Macrophages were sorted-purified as $CD45^+F480^+Siglec$ $F^+$ $CD11c^+MHCII^+$. Monocytes were sort-purified as $CD45^+$ $CD11b^+CCR2GFP^+NK1.1^-CD11c^-$. BM-derived mast cells were sort-purified as $CD3^-$ $CD19^-$ $CD49b^-$ $CD200R^+$ $c-Kit^+$ and BM-derived basophils as $CD3^-$ $CD19^-$ $c-Kit^-$ $CD200R^+$ $CD49b^+$. BM-derived cells were sort-purified on day 7 post-culture. Purity for all cell populations were determined to be 98% or greater. RNA was extracted using Qiagen RNeasy Kit, and amplified using Ambion MessageAmp II aRNA Amplification Kit. Relative mRNA levels were determined by real-time-PCR. RNA was reverse transcribed using High Capacity cDNA Reverse Transcription Kit (Applied Biosystems). Taq Man Fast Universal PCR Master Mix (2×) No Amp and TaqMan probes (Applied Biosystems) for each gene were used.

Murine Mast Cell and Basophil Cultures

BM cells were isolated from the femur of WT mice and cultured in the presence of 10 ng/mL of IL-3 and vehicle (1:10 DMSO to RPMI complete media) or 30 µg/mL MZ. Fresh IL-3 with either vehicle or MZ were added daily, and mast cell and basophil populations were evaluated on day 7 post-culture.

Murine Macrophage Cultures

BM cells were isolated from the femur of WT mice and cultured in the presence of 30% L-cell supernatant and vehicle (1:10 DMSO to RPMI complete media) or 30 µg/mL MZ. Fresh macrophage medium with either vehicle or MZ was added daily and macrophage cell populations were evaluated on day 5 post-culture.

*Trichinella spiralis* Infection and IL-3C Treatment

Methods for maintenance, recovery, infection and isolation of *Trichinella* larvae were performed as previously described (Urban, et al., 2000. *J Immunol* 164:2046-2052). Mice were infected with 500 *Trichinella* muscle larvae by oral gavage and were treated with vehicle (1:5 DMSO to PBS) or 2-3 mg of MZ i.p. daily; mice were sacrificed between 10-11 days post-infection. At necropsy, single cell suspensions of mLNs and spleens were prepared as previously described (Giacomin, et al., 2012. *Journal of immunology* (Baltimore, Md.: 1950) 189:4371-4378) for basophil and mast cell analysis. Blood was collected and serum was isolated for analysis of Mcpt1 and IgE. Sections (1 cm) of small intestine (jejunum) were collected for real-time PCR and histological analysis. Remaining sections of small intestine were slit lengthwise, rinsed in PBS, and placed in HBSS for 4 hours at 37° C. and adult worms were quantified by microscopic analysis as previously described (Urban, et al., 2000. *J Immunol* 164:2046-2052). Rag1$^{-/-}$ mice were injected (i.p.) with a combination of recombinant IL-3 (1 µg) and α-IL-3 antibody (0.5 µg) (BioLegend: clone MP2-8F8) in 200 µl PBS every 3 days for 7-10 days. IL-3C-treated mice were treated with MZ (2 mg) or vehicle (DMSO) every day.

RNA Isolation and Quantitative Real-Time PCR Analysis

RNA from sections of small intestine was isolated by homogenization in TRIzol (Invitrogen) followed by phenol-chloroform extraction and isopropanol precipitation. cDNA was generated per standard protocol with Superscript reverse transcriptase (Invitrogen) and used as input for real-time PCR. Real-time data were analyzed using the ΔΔCT method using SYBR Green chemistry (Applied Biosystems) with f-actin serving as the endogenous housekeeping gene. All reactions were run on an ABI 7500 Fast Real-Time PCR System (Applied Biosystems). Samples were normalized to naïve controls. The following QuantiTech primer assays from Qiagen were used: Mcpt1 (QT00157864), IL-4 (QT00160678), IL-9 (QT00107555), Arg1 (QT00134288), Retnla (QT00254359), Car1 (QT01058113) and Car2 (QT00494592).

T Cell Stimulations and ELISAs.

Single cell suspensions were made from mesenteric, or skin draining lymph nodes. Lymph node cells were cultured in RPMI complete medium and treated with and without anti-CD3 (BD Pharmingen: clone 145-2C11) and anti-CD28 antibodies (BD Pharmingen: clone 37.51) for 72 hours. Standard sandwich ELISA (eBioscience) was performed to measure IL-4 (clones 11B11 and BVD6-24G2), IL-5 (clones TRFK5 and TRFK4) and IL-13 (clones eBio13A and eBio1316H) levels in the cell-free supernatants. Serum quantities of Mcpt1 and IgE were measured by commercial sandwich ELISA kits (BD Biosciences, eBioscience).

Atopic Dermatitis Like-Disease

Mice were treated once a day topically with 2 nmol of MC903 (calcipotriol, Tocris Bioscience) in 20 µl of ethanol for 6 days as described previously (Kim, et al., 2013. *Sci Transl Med* 5:170ra116). MC903-treated mice were treated with vehicle (1:5 DMSO to PBS) or 2-3 mg of MZ i.p. daily and sacrificed on day 7 post-treatment.

Preparation of *Aspergillus fumigatus* Conidia

*A. fumigatus* strain Af293 was grown on glucose minimal media (GMM) agar plates for 3 days or Sabouraud dextrose agar (SDA) for 7-10 days at 37° C., respectively. Conidia were harvested by adding 0.01% Tween 80 to plates and gently scraping conidia from the plates using a cell scraper. Conidia were then filtered through sterile Miracloth, were washed and resuspended in phosphate buffered saline (PBS), and counted on a hemocytometer. FLARE conidia were prepared as previously described (Espinosa, et al., 2014. *PLoS Pathog* 10:e1003940). Mice were challenged with $5 \times 10^7$ *A. fumigatus* conidia intratracheally (i.t.) as described previously (Espinosa, et al., 2014. *PLoS Pathog* 10:e1003940). Mice were treated with vehicle (1:5 DMSO to PBS) or 2-3 mg of MZ i.p. daily and sacrificed 72 hours post-infection. Bronchoalveolar lavage (BAL) fluid was collected by washing the lungs with 2 mL of PBS containing 0.05M EDTA. After collection of the BAL fluid, lung samples were minced in RPMI containing 100 units/mL of collagenase (Gibco) and incubated at 37° C. for 60 minutes, disrupted and filtered. Subsequently, red blood cells were lysed using a Tris ammonium chloride solution. Analysis of neutrophils was conducted using a panel of cell surface markers: CD45, CD11b, and Ly6G as previously described (Espinosa, et al., 2014. *PLoS Pathog* 10:e1003940). To deplete lung neutrophils, mice were injected with 500 µg of anti-Ly6G antibody (BioXcel: clone 1A8) i.p followed by another dose of 100 µg i.t. (Espinosa, et al., 2014. *PLoS Pathog* 10:e1003940).

Food Allergy

Food allergy-like disease was initiated as previously described (Noti, et al., 2014. *J Allergy Clin Immunol* 133: 1390-1399, 1399 e1391-1396). Briefly, mice were treated daily with 2 nmol of MC903 (calcipotriol; Tocris Bioscience, Bristol, United Kingdom) in 20 µl of 100% ethanol on ears in the presence of 100 µg of ovalbumin (OVA) daily for 14 days. As a vehicle control, the same volume of EtOH and OVA was applied. All mice were challenged intragastrically with 50 mg of OVA on days 14 to 17.5. Mice were sacrificed on day 18. Groups of mice were treated with vehicle (1:5 DMSO to PBS) or 2-3 mg of MZ i.p. daily until sacrifice.

Bone Marrow Chimeras

Mice were lethally irradiated (1050 rad) and reconstituted with $1 \times 10^6$ WT BM cells, $1 \times 10^6$ Car2$^{-/-}$ BM cells, or a mix of $5 \times 10^5$ WT and $5 \times 10^5$ Car2$^{-/-}$ BM cells. Mice were allowed to reconstitute for a period of 8 weeks.

Mouse Embryonic Stem Cells Culture

R1 mouse embryonic stem cells (ESCs) (Nagy, et al., 1993. *Proceedings of the National Academy of Sciences of the United States of America* 90:8424-8428) were kindly provided by Dr. Andras Gravy (Lunenfeld-Tanenbaum Research Institute, Mount Sinai Hospital, Toronto, Ontario) and cultured as described previously (Lin, et al., 2011. *Methods in molecular biology* (Clifton, N.J.) 690:31-56). Briefly, irradiated mouse embryonic fibroblasts (MEFs) (R&D systems laboratories) were cultured according to the manufacturer's protocol. One day later, $1.0 \times 10^6$ ESCs were cultured over MEFs for approximately 4 days until they reached a confluence of approximately 80-90%. Medium was replaced every 24 hrs. ESCs and MEFs were detached using StemPro® Accutase® (Thermo Fisher Scientific) following the manufacturer's instructions until cell suspensions were obtained. Cell suspension was then plated on gelatin-coated vessels for 45 minutes to separate MEFs from ESCs.

CRISPR/Cas9 Transfections

CRISPR/Cas9 genome editing was performed as described previously (Kim, et al., 2014. *Genome research* 24:1012-1019). Cas9 nuclease (1 µg/µl, Invitrogen) was incubated with in vitro transcribed gRNAs (240 ng/µl, Invitrogen) targeting the gene encoding Car1 (AGAATATCTAGTTCCATCCA (SEQ ID NO: 1)) according to manufacturer's instructions. $1.0 \times 10^6$ ESCs were washed once with 1×PBS and resuspended in 50 µl of resuspension buffer. 5 µl of ESC suspension was mixed with 7 µl of Cas9/gRNA complexes and cells were electroporated using the Neon® Transfection System (Invitrogen) (1300V, 10 width, 3 pulses). Mock-transfected control cells were electroporated with Cas9 protein only. ESCs were cultured over MEFs immediately after transfection and until they reached a confluence of 80-90%. Genome targeting efficiency was determined as previously described (Guschin, et al., 2010. *Methods in molecular biology* (Clifton, N.J.) 649:247-256). Briefly, genomic DNA was isolated using the QIAamp DNA mini kit (Qiagen, Valencia CA). Then, a 600 bp gene region containing the targeted sequence for car1 was amplified by PCR (Fp: GCTCTGTGATTAAAGTCCAG (SEQ ID NO:2), Rp: TTCCATCGTGCACAAGGCA (SEQ ID NO:3)). The PCR product was reannealed and incubated with 1 µl of T7 endonuclease (New England Biolabs). PCR products were run on a 2% agarose gel and the band's percentage intensity was analyzed using the Image Lab™ software (Bio-Rad). Following genome targeting efficiency assays, aliquots of cells from this parent culture of approximately $3.0 \times 10^6$ cell were removed and plated for developmental assays.

Mast Cell and Macrophage Differentiation from ESCs

Mast cell and macrophage differentiation was performed as previously described (Kovarova, et al., 2012. *Current protocols in immunology*/edited by John E. Coligan . . . [et al.] Chapter 22: Unit 22F.10.21-16). Briefly, ESCs were cultured with 9 mL of Differentiation Medium (α-MEM medium supplemented with 15% ES-qualified FBS, penicillin/streptomycin, 5% of protein free hybridoma medium, Insulin Transferrin Selenium supplement, 1-thioglycerol and ascorbic acid) on petri dishes for 10 days replacing the medium every 3 days, in order to generate embryonic bodies. Embryonic bodies were dissociated as described previously (Kovarova, et al., 2012. *Current protocols in immunology*/edited by John E. Coligan . . . [et al.] Chapter 22: Unit 22F.10.21-16) and washed. $5.0 \times 10^5$ cells were plated and treated with recombinant IL-3 (10 ng/mL) to generate mast cells or with 30% of L-sup to induce macrophage differentiation. Media was replaced every 48 hrs. After 3 weeks of culture, mast cell and macrophage populations were analyzed by flow cytometry.

Human Mast Cell Cultures

Blood from healthy human donors was obtained from the New York Blood Center under protocols approved by the Rutgers Institutional Review Boards (IRB). Peripheral blood cells were isolated using a Ficoll gradient. $CD34^+$ cells were purified using a CD34 MicroBead isolation kit according to the manufacturer's protocol (Miltenyi Biotec, 130-048-702). $25$-$50 \times 10^3$ $CD34^+$ cells were placed in methocult (H4236) supplemented with stem cell factor (SCF), TL-6 and TL-3 as described previously (Saito, et al., 2006. *Nat Protoc* 1:2178-2183). Mast cell populations were evaluated on day 14 post-culture.

Statistics

Results are shown as mean±standard deviation. Statistical analysis was performed using Student's t-tests in GraphPad Prism version 6.

Figure 5:
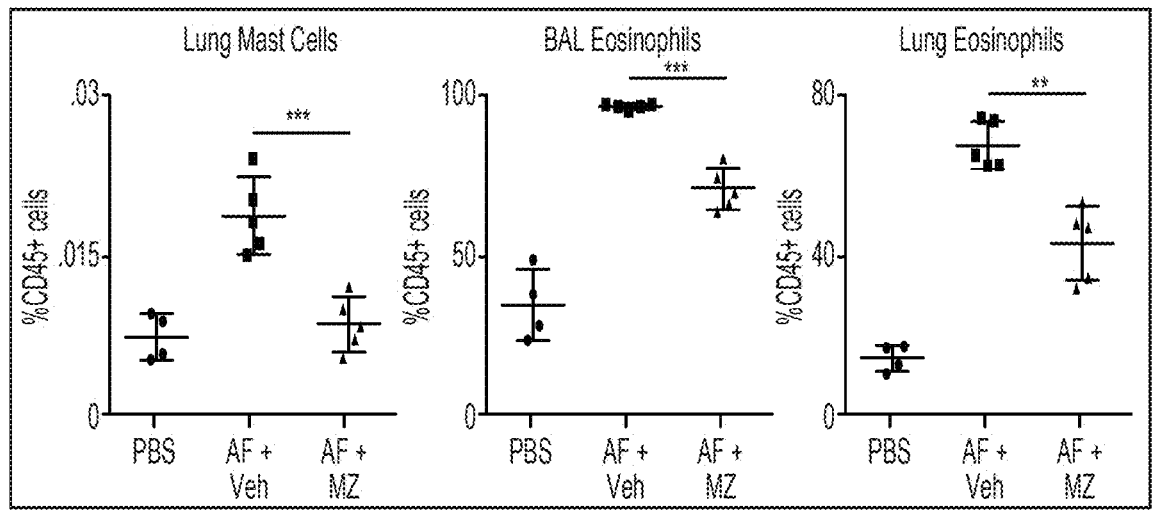
FIG. 5. Mice were treated with phosphate buffered saline (PBS) or $A.$ $fumigatus$ extract (AF) intranasally. Mice treated with AF were also treated with vehicle (Veh) or MZ. After three weeks of treatment, lung tissue and BAL were collected. Single cell suspensions of lung tissue were made and mast cell and eosinophil responses were quantified by flow cytometric analysis. Eosinophils were also quantified in BAL fluid by flow cytometric analysis. Statistical analysis was performed using a Student's t-test. (, $p<0.01$) (*, $p<0.001$).

Example 2. Car Inhibitor Methazolamide Significantly Reduces Mast Cell Response and Eosinophil Influx in a Murine Model of Asthma As described in other studies herein, targeting carbonic anhydrase (Car) enzymes with the inhibitor methazolamide (MZ) has been demonstrated to be sufficient to prevent murine and human mast cell development from progenitor cells. Further, this data demonstrate that treating mice with MZ was sufficient to prevent inflammatory mast cell responses following *Trichinella spiralis* infection or the induction of food allergy-like disease. Collectively, these studies suggest that Car enzymes can be targeted therapeutically to treat mast cell-mediated inflammation. Mast cells are recognized for their important role in the induction of several forms of allergic inflammation at distinct anatomical sites including the gut and lung (Voehringer, *Nat Rev Immunol* 13, 362-375 (2013)). The data described herein has demonstrated that Car enzyme inhibition is sufficient to alleviate inflammatory mast cell responses in the intestines, but whether this pathway can be targeted to prevent mast cell responses in the lung remains unknown. Therefore, it was also sought to be determined if Car enzyme inhibition was sufficient to prevent inflammatory mast cell responses and eosinophilic airway inflammation in the context of a murine model of allergic asthma (Ghosh, et al., *Front Pharmacol* 4, 8 (2013)). To test this, a clinically relevant model of *Aspergillus fumigatus*-induced allergic airway inflammation that is known to be dependent on mast cell activation was employed (Mathias, C. B., et al., *J Immunol* 182, 2416-2424 (2009)). As published previously (Mathias, C. B., et al., *J Immunol* 182, 2416-2424 (2009)), mice challenged intranasally with fungal extract exhibited significantly increased mast cell responses in the lung and eosinophilia in the bronchiole alveolar lavage (BAL) fluid and lung tissue (FIG. 5). Importantly, mice treated with MZ exhibited significantly reduced pulmonary mast cell responses and eosinophilic airway inflammation (FIG. 5). These data are consistent with the previous studies demonstrating that Car enzymes can be targeted to alleviate mast cell-mediated intestinal inflammation, and suggest that this pathway can also be targeted to lessen allergic airway inflammation.

Material and Methods:

*Aspergillus*-induced allergic asthma. Mice were challenged with *Aspergillus fumigatus* allergic extract as previously described (Mathias, C. B., et al., *J Immunol* 182, 2416-2424 (2009)). Briefly, mice were challenged (intranasally) 3 times a week for 3 weeks with 50 µl of aqueous *Aspergillus fumigatus* Allergenic Extract (Greer laboratories: item #M3). After 3 weeks mice were sacrificed and BAL and lungs were processed as previously described (Espinosa, V., et al., *PLoS Pathog* 10, e1003940 (2014)).

Figure 6A:
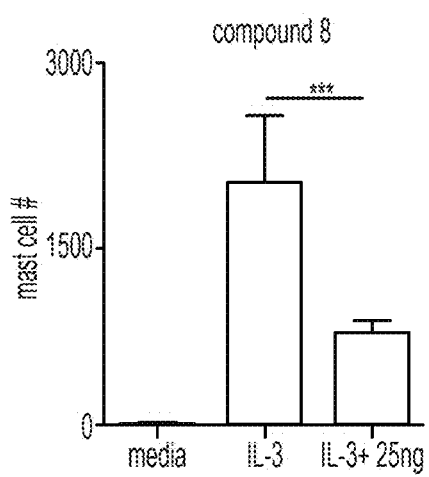
FIGS. 6A-6B. Bone marrow-resident progenitor cells were cultured in media, media treated with IL-3 (10 ng/ml), media treated with IL-3 and compound 8 (25 ng/ml) (FIG. 6A) or, media treated with IL-3 and compound 16 (25, 50, or 75 ng/ml) (FIG. 6B). On day 7 post-culture mast cells were identified by flow cytometric analysis. Results are representative of 2 independent experiments with at least 4 technical replicated per experiment. Statistical analysis was performed using a Student's t-test. (*, $p<0.05$) (***, $p<0.001$).
Figure 6B:
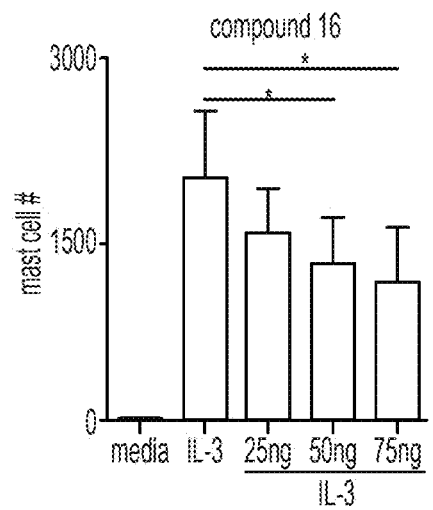

Example 3. Selective Car1 Inhibitors Sufficient to Inhibit Mast Cell Development The studies described herein demonstrate that the Car enzyme inhibitor MZ is sufficient to prevent in vitro and in vivo mast cell responses. Further, it is illustrated that genetically editing Car1 in stem cells via CRISPR/Cas9 technology decreases their capacity to develop into mature mast cells. These data provoke that hypothesis that Car1 operates as a positive regulator of mast cell development. However, whether inhibitors that selectively target Car1 can be used to inhibit mast cell development was unknown. The Car enzyme inhibitors compound 8 and compound 16 are reported to preferentially inhibit Car1 but have little to no effects on other Car family members (Talibov, et al., *J Med Chem* 59, 2083-2093 (2016)). Therefore, it was sought to be determined whether compound 8 and/or compound 16 could inhibit mast cell development from progenitor cell populations. To test this, the mast cell developmental assay was employed and bone marrow-resident progenitor cells were treated with IL-3 to promote mast cell development. As expected, treating progenitor cells with IL-3 resulted in increased mast cell populations (FIG. 6A-6B). Critically, when progenitor cells were treated with IL-3 and 25 ng/ml of compound 8, significantly fewer mast cells were recovered (FIG. 6A). Although compound 16 did not significantly inhibit mast cell development at 25 ng/ml, significantly fewer mast cells were recovered from cultures treated with IL-3 and 50 ng/ml or 75 ng/ml of compound 16 (FIG. 6B). Collectively, these data suggest that enzyme inhibitors known to selectively target Car1 are sufficient to prevent mast cell development and could be employed to treat mast cell mediated inflammation while reducing the off-target effects of a more global inhibitor that alters the activation state of other Car enzymes family members.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for treating allergic asthma comprising administering to a mammal in need thereof an effective amount of a carbonic anhydrase (Car) enzyme inhibitor wherein the Car enzyme inhibitor is methazolamide.

2. The method of claim 1, further comprising administering one or more additional therapeutic agent(s).

3. The method of claim 2, wherein the one or more additional therapeutic agent(s) is an anti-histamine, a steroid, an anti-IgE therapy, a decongestant, a bronchodilator, a mast cell stabilizer, a leukotriene modifier and/or an immunotherapy.

4. The method of claim 2, wherein the one or more additional therapeutic agent(s) is an anti-histamine selected from the group consisting of Acrivastine, Azelastine, Bilastine, Brompheniramine, Buclizine, Bromodiphenhydramine, Carbinoxamine, Cetirizine, Chlorpromazine, Cimetidine, Cyclizine, Chlorphenamine, Chlorodiphenhydramine, Clemastine, Cyproheptadine, Desloratadine, Dexbrompheniramine, Dexchlorpheniramine, Dimetindene, Diphenhydramine, Ebastine, Embramine, Famotidine, Fexofenadine, Hydroxyzine, Lafutidine, Levocetirizine, Loratadine, Nizatidine, Olopatadine, Phenindamine, Pheniramine, Phenyl-

SEQUENCE LISTING

<160> NUMBER OF SEQ ID NOS: 3

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
agaatatcta gttccatcca                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctctgtgat taaagtccag                                              20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ttccatcgtg cacaaggca                                               19 toloxamine, Promethazine, Pyrilamine, Ranitidine, Roxatidine, Rupatadine, Tiotidine, Tripelennamine and Triprolidine.

5. The method of claim 1, wherein the mammal is a human.

6. The method of claim 1, wherein the Car enzyme inhibitor reduces pulmonary mast cell responses.

7. The method of claim 1, wherein the Car enzyme inhibitor reduces allergic airway inflammation.

8. The method of claim 1, wherein the Car enzyme inhibitor reduces eosinophilic airway inflammation.

* * * * *